United States Patent
Tanigawa et al.

(10) Patent No.: US 7,149,277 B2
(45) Date of Patent: *__Dec. 12, 2006__

(54) CORRECTION COEFFICIENT CALCULATING METHOD FOR X-RAY CT SYSTEMS, BEAM HARDENING POST-PROCESSING METHOD THEREFOR, AND X-RAY CT SYSTEM

(75) Inventors: Shunichiro Tanigawa, Tokyo (JP); Masatake Nukui, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 139 days.

This patent is subject to a terminal disclaimer.

(21) Appl. No.: 10/816,626

(22) Filed: Apr. 2, 2004

(65) Prior Publication Data

US 2004/0196960 A1  Oct. 7, 2004

(30) Foreign Application Priority Data

Apr. 4, 2003   (JP) ............................ 2003-101277

(51) Int. Cl.
*A61B 6/03* (2006.01)
(52) U.S. Cl. ....................................... 378/18
(58) Field of Classification Search ................ 378/18, 378/207
See application file for complete search history.

(56) References Cited

U.S. PATENT DOCUMENTS

| | | | |
|---|---|---|---|
| 4,352,020 A | 9/1982 | Horiba et al. | |
| 4,870,666 A | 9/1989 | Lonn | |
| 5,095,431 A | 3/1992 | Feldman et al. | |
| 5,222,021 A | 6/1993 | Feldman et al. | |
| 5,774,519 A | 6/1998 | Lindstrom et al. | |
| 5,867,553 A | 2/1999 | Gordon et al. | |
| 5,953,444 A | 9/1999 | Joseph et al. | |
| 6,430,252 B1 | 8/2002 | Reinwand et al. | |
| 6,438,197 B1 | 8/2002 | Stierstorfer | |
| 6,505,966 B1 | 1/2003 | Guru | |
| 6,507,633 B1 | 1/2003 | Elbakri et al. | |
| 6,944,258 B1 * | 9/2005 | Nukui et al. ................... | 378/4 |
| 2003/0063704 A1 | 4/2003 | Lang | |

FOREIGN PATENT DOCUMENTS

FR   2 656 697   7/1991
JP   07 171145 A   7/1995

OTHER PUBLICATIONS

Computer translation of FR 2656697 A.*
Mitchell M. Goodsitt, Beam Hardening errors in post-processing dual energy quantitative computed tomography, 1039 Med. Phys. 22 (7), Jul. 1995, Woodbury, NY, US.
Partial European Search Report, Docket 16CT148821, European Patent Application No. 04 251 879.5, 6 pgs.

* cited by examiner

*Primary Examiner*—Edward J. Glick
*Assistant Examiner*—Chih-Cheng Glen Kao
(74) *Attorney, Agent, or Firm*—Carl B. Horton; Armstrong Teasdale, LLP

(57) ABSTRACT

An object of the present invention is to calculate a more accurate beam-hardening correction coefficient. A phantom having an oblong section or a phantom having an annular (sector) section and a uniform thickness is positioned in an X-ray CT system, and scanned from plural directions in order to acquire a plurality of views. The results of the scan are used to calculate a correction coefficient that is used to correct projection information to be acquired from a subject.

8 Claims, 14 Drawing Sheets

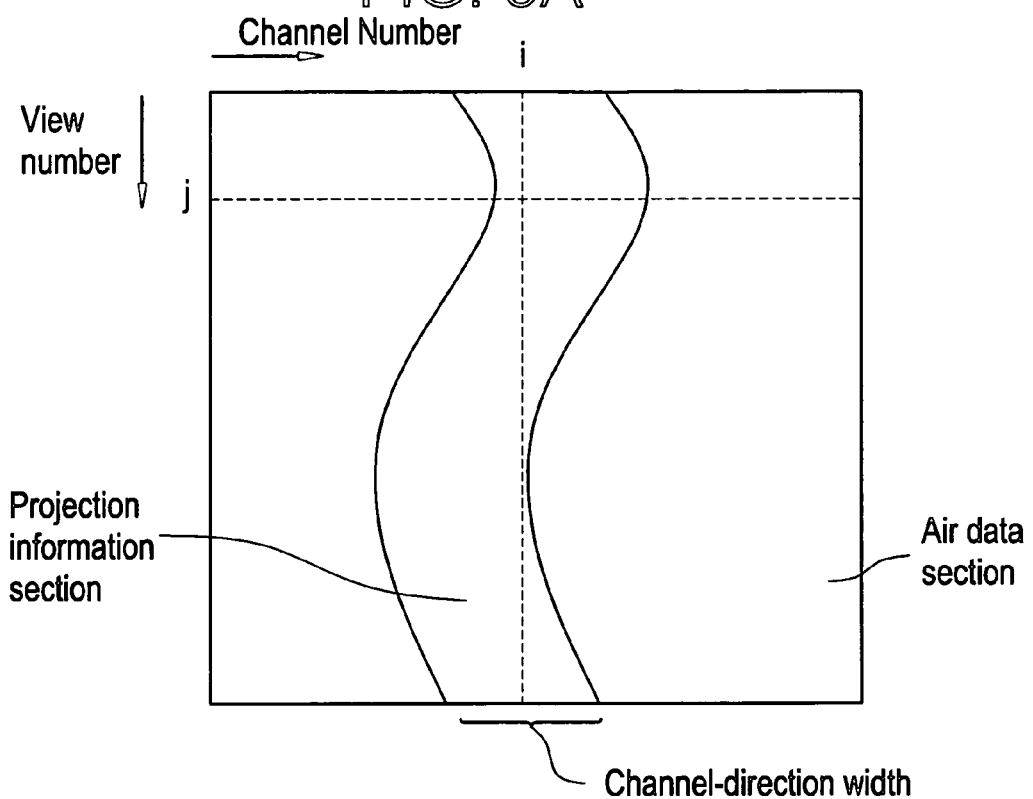
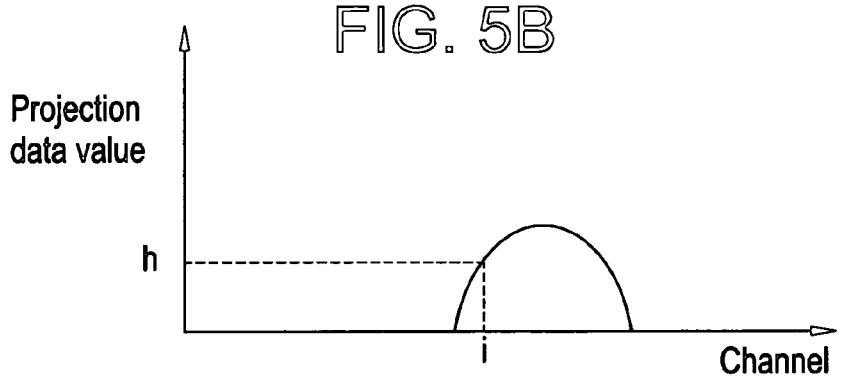
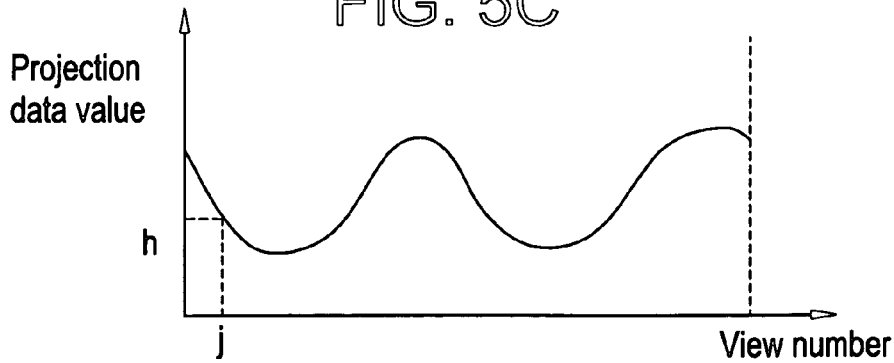

obese trunk thin trunk head chest abdomen

CORRECTION COEFFICIENT CALCULATING METHOD FOR X-RAY CT SYSTEMS, BEAM HARDENING POST-PROCESSING METHOD THEREFOR, AND X-RAY CT SYSTEM

CROSS REFERENCE TO RELATED APPLICATIONS

This application claims the benefit of Japanese Application No. 2003-101277 filed Apr. 4, 2003.

BACKGROUND OF THE INVENTION

The present invention relates to a beam hardening (BH) method for correcting (calibrating) the intensity of X-rays transmitted by a subject on the basis of phantom data, and a computed tomography (CT) system adopting the beam hardening method.

An X-ray CT system will be taken as an example of a CT system.

An X-ray source employed in an X-ray CT system generates X-rays that fall within a certain energy range. An absorption coefficient for X-rays to be transmitted by a subject depends on the energy in the X-rays. The larger a length in the subject over which X-rays are transmitted, the higher the average energy in transmitted X-rays. This phenomenon is referred to as a beam-hardening (BH) effect. Consequently, a proportional relationship is not established between the intensity of transmitted X-rays, that is, a projection information value produced from a signal detected by an X-ray detector included in the X-ray CT system, and the length in the subject over which X-rays are transmitted, but a linear relationship is.

The beam-hardening effect causes the cupping effect signifying that the intensity of the center of a reconstructed image produced by the X-ray CT system gets lower. A signal detected by an X-ray detector must therefore be corrected. A correction coefficient to be used to correct projection information values based on which a reconstructed image is produced to exhibit a uniform intensity is calculated in relation to each of the channels of the X-ray detector, whereby the correction is achieved.

For higher-precision correction, phantoms are used. Such phantoms include multiple cylindrical phantoms having circular sections and different diameters that are large enough to generally cover the entire field of view (FOV) (scan field) defined in the center of an X-ray field. Projection information acquired from the phantoms is used to precisely correct a correction coefficient (refer to, for example, Patent Document 1).

[Patent Document 1]
Japanese Unexamined Patent Publication No. Hei 7(1995)-171145

According to the foregoing method, when the projection information is acquired, the plurality of phantoms that has circular sections and different diameters must be disposed. Since the phantoms are large in size, disposing them is labor-intensive. Since scan must be repeated, much time is required. Besides, the projection information values cannot be corrected highly precisely in consideration of a non-linear effect attributable to the aforesaid beam-hardening effect.

Furthermore, in order to correct projection information values highly precisely, many different projection information values are needed in relation to each of the channels of an X-ray detector. Therefore, lots of phantoms that have circular sections and different diameters must be disposed in the center of a scan field between an X-ray tube and the X-ray detector, and then scanned.

In particular, in order to acquire calibration information for the X-ray CT system, two or three phantoms that have circular sections and diameters ranging from 20 cm to 50 cm are used and scanned for 100 min or more. The scan that persists for 100 min or more must be performed exclusively for precise correction. Thus, the calibration requires too much time and labor.

SUMMARY OF THE INVENTION

An object of the present invention is to provide a beam-hardening post-processing method for acquiring calibration information that permits ready and highly precise correction of projection data in terms of the beam-hardening effect relative to each of the channels of an X-ray detector, on which the projection data is detected, while taking account of even a non-linear effect, and to provide an X-ray CT system.

According to the first aspect of the present invention, there is provided a correction coefficient calculating method for X-ray CT systems. Herein, a phantom having an oblong section is positioned in a scan field between an X-ray tube and an X-ray detector, and scanned from plural directions in order to acquire a plurality of views. Based on the results of the scan, a correction coefficient used to correct projection information to be acquired from a subject is calculated.

According to the second aspect of the present invention, there is provided a correction coefficient calculating method for X-ray CT systems. Herein, a phantom having an annular section and a nearly uniform thickness is positioned in a scan field between an X-ray tube and an X-ray detector, and scanned from one or plural directions in order to acquire a plurality of views. Views indicating transmitted doses that exceed a predetermined value are excluded from among the plurality of views in order to sample the effective results of the scan. Based on the effective results of the scan, a correction coefficient used to correct projection information acquired from a subject is calculated.

According to the third aspect of the present invention, there is provided a correction coefficient calculating method for X-ray CT systems. Herein, a first phantom having an oblong section is positioned in a scan field between an X-ray tube and an X-ray detector, and scanned from one or plural directions in order to acquire a plurality of views. Based on the results of the scan, a first correction coefficient used to correct projection information to be acquired from a subject is calculated. A second phantom having an annular section and a nearly uniform thickness is positioned in the scan field and scanned from one or plural directions in order to acquire a plurality of views. Views indicating transmitted doses that exceed a predetermined value are excluded from the plurality of views in order to sample the effective results of the scan. Based on the sampled effective results of the scan, a second correction coefficient used to correct projection information to be acquired from a subject is calculated. Based on the first and second correction coefficients, a final correction coefficient used to correct projection information to be acquired from a subject is calculated.

According to the fourth aspect of the present invention, there is provided a correction coefficient calculating method for X-ray CT systems. Herein, a first phantom having an oblong section is positioned in a scan field between an X-ray tube and an X-ray detector, and scanned from one or plural directions in order to acquire a plurality of views. Based on the results of the scan, a first correction coefficient used to correct projection information to be acquired from a subject is calculated. A second phantom having an annular section and a nearly uniform thickness is positioned in the scan field, and scanned from one or plural directions in order to acquire a plurality of views. Views indicating transmitted doses that exceed a predetermined value are excluded from the plurality of views in order to sample the effective results of the scan. Based on the sampled effective results of the scan, a second correction coefficient used to correct projection information acquired from a subject is calculated. A third phantom having a circular section is positioned in the scan field, and scanned from one or plural directions in order to acquire a plurality of views. Based on the results of the scan, a third correction coefficient used to correct projection information to be acquired from a subject is calculated. Based on the first to third correction coefficients, a final correction coefficient that is used to correct projection information acquired from a subject is calculated.

According to the fifth aspect of the present invention, there is provided an X-ray CT system in which projection information acquired from a subject is corrected using a correction coefficient that is calculated according to any of the foregoing correction coefficient calculating methods.

According to the sixth aspect of the present invention, there is provided a beam-hardening post-processing method for X-ray CT systems. Herein, a phantom having an oblong section is positioned in a scan field between an X-ray tube and an X-ray detector, and scanned from one or plural directions in order to acquire a plurality of views. First projection information is used to produce a sinogram. The first projection information is corrected in terms of the beam-hardening effect in order to produce second projection information. A first function is fitted to the second projection information, whereby third projection information is produced. A second function is fitted to the third projection information values. Herein, the third projection information values are provided as functions having as independent variables second projection information values sampled in relation to all the views and each of the channels of the X-ray detector constituting the second projection information. A correction coefficient provided as the second function is used to correct projection information acquired from a subject who lies in the scan field.

According to the seventh aspect of the present invention, there is provided a beam-hardening post-processing method for X-ray CT systems. Herein, a phantom having an annular section and a nearly uniform thickness is positioned in a scan field between an X-ray tube and an X-ray detector which are included in an X-ray CT system, and scanned from one or plural directions in order to acquire a plurality of views. One sinogram is produced based on projection information. The first projection information is corrected in terms of the beam-hardening effect in order to produce second projection information. A first function is fitted to the second projection information in order to produce third projection information. A second function is fitted to the third projection information values. Herein, the third projection information values are provided as functions having as independent variables second projection information values that are sampled in relation to all the views and each of the channels of the X-ray detector. A correction coefficient provided as the second function is used to correct projection information acquired from a subject who is positioned in the scan field.

According to the eighth aspect of the present invention, there is provided a beam-hardening post-processing method for X-ray CT systems. Herein, a first phantom having an oblong section is positioned in a scan field between an X-ray tube and an X-ray detector, and scanned from one or plural directions in order to produce a plurality of views. One sinogram is produced based on first projection information. The first projection information is corrected in terms of the beam-hardening effect in order to produce second projection information. A first function is fitted to the second projection information in order to produce third projection information. A second function is fitted to the third projection information values. Herein, the third projection information values are provided as functions having as independent variables the second projection information values that are sampled in relation to all the views and each of the channels of the X-ray detector constituting the second projection information. A first correction coefficient is calculated as the second function. A second phantom having an annular section and a nearly uniform thickness is positioned in the scan field, and scanned from one or plural directions in order to produce a plurality of views. Projection information is corrected in terms of the beam-hardening effect in order to produce second projection information. A first function is fitted to the second projection information, whereby third projection information is produced. A second function is fitted to the third projection information values. Herein, the third projection information values are provided as functions having as independent variables the second projection information values that are sampled in relation to all the views and each of the channels of the X-ray detector constituting the second projection information. A second correction coefficient is calculated as the second function. Final correction coefficients to be used to finally correct projection information to be acquired from a subject are calculated based on the first and second correction coefficients. The final correction coefficients are used to correct projection information acquired from a subject who lies in the scan field.

According to the ninth aspect of the present invention, there is provided a beam-hardening post-processing method for X-ray CT systems. Herein, a first phantom having an oblong section is positioned in a scan field between an X-ray tube and an X-ray detector, and scanned from one or plural directions in order to acquire a plurality of views. First projection information acquired from the first phantom is used to produce one sinogram. The first projection information is corrected in terms of the beam-hardening effect in order to produce second projection information concerning the first phantom. A first function is fitted to the second projection information in order to produce third projection information concerning the first phantom. A second function is fitted to the third projection information values concerning the first phantom. At this time, the third projection information values are provided as functions having as independent variables the second projection information values concerning the first phantom that are sampled in relation to all the views and each of the channels of the X-ray detector constituting the second projection information. Consequently, a first correction coefficient concerning the first phantom is calculated as the second function. Thereafter, a second phantom having an annular section and a nearly uniform thickness is positioned in the scan field, and scanned from one or plural directions in order to acquire a plurality of views. Projection information is used to produce one sinogram. The projection information acquired from the second phantom is corrected in terms of the beam-hardening effect in order to produce second projection information concerning the second phantom. A first function is fitted to the second projection information in order to produce third projection information concerning the second phantom. A second function is fitted to the third projection information values concerning the second phantom. At this time, the third projection information values are provided as functions having as independent variables the second projection information values concerning the second phantom that are sampled in relation to all the views and each of the channels of the X-ray detector constituting the second projection information. Consequently, a second correction coefficient concerning the second phantom is calculated as the second function. Final correction coefficients to be used to correct projection information to be acquired from a subject are calculated based on the first and second correction coefficients. The final correction coefficients are used to correct projection information acquired from a subject who lies in the scan field.

According to the tenth aspect of the present invention, there is provided a beam-hardening post-processing method for X-ray CT systems. Herein, a first phantom having an oblong section is positioned in a scan field between an X-ray tube and an X-ray detector, and scanned from one or plural directions in order to acquire a plurality of views. First projection information acquired from the first phantom is used to produce one sinogram.

The first projection information is corrected in terms of the beam-hardening effect in order to produce second projection information concerning the first phantom. A first function is fitted to the second projection information in order to produce third projection information. A second function is fitted to the third projection information values concerning the first phantom. At this time, the third projection information values concerning the first phantom are provided as functions having as independent variables the second projection information values that are sampled in relation to all the views and each of the channels of the X-ray detector constituting the second projection information. Consequently, a first correction coefficient concerning the first phantom is calculated as the second function. Thereafter, a second phantom having an annular section and a nearly uniform thickness is positioned in the scan field, and scanned from one or plural directions in order to produce a plurality of views. Projection information is used to produce one sinogram. The first projection information acquired from the second phantom is corrected in terms of the beam-hardening effect in order to produce second projection information concerning the second phantom. A first function is fitted to the second projection information in order to produce third projection information concerning the second phantom. A second function is fitted to the third projection information values concerning the second phantom. At this time, the third projection information values are provided as functions having as independent variables the second projection information values concerning the second phantom that are sampled in relation to all the views and each of the channels of the X-ray detector constituting the second projection information. Consequently, a second correction coefficient concerning the second phantom is calculated as the second function. Thereafter, a third phantom having a circular section is positioned in the scan field, and scanned from one or plural directions in order to acquire a plurality of views. First projection information acquired from the third phantom is used to produce one sinogram. The first projection information is corrected in terms of the beam-hardening effect in order to produce second projection information concerning the third phantom. A first function is fitted to the second projection information in order to produce third projection information concerning the third phantom. A second function is fitted to the third projection information values concerning the third phantom. At this time, the third projection information values are provided as functions having as independent variables the second projection information values concerning the third phantom that are sampled in relation to all the views and each of the channels of the X-ray detector constituting the second projection information. Consequently, a third correction coefficient concerning the third phantom is calculated as the second function. Final correction coefficients to be used to correct projection information to be acquired from a subject are calculated based on the first to third correction coefficients. The final correction coefficients are then used to correct projection information acquired from a subject who lies in the scan field.

According to the eleventh aspect of the present invention, there is provided an X-ray CT system in which projection information acquired from a subject is corrected using a correction coefficient calculated according to any of the foregoing beam-hardening post-processing methods.

According to the present invention, a correction coefficient used to correct projection information can be calculated according to the shape or region of a subject. When the correction coefficient is used to correct projection information acquired from a subject, a more accurate tomographic image can be produced.

According to the present invention, a correction coefficient adaptable to various subjects can be calculated. When the correction coefficient is used to correct projection information acquired from subjects, more accurate tomographic images of various subjects can be produced.

Further objects and advantages of the present invention will be apparent from the following description of the preferred embodiments of the invention as illustrated in the accompanying drawings.

BRIEF DESCRIPTION OF THE DRAWINGS

FIG. 5(A) to FIG. 5(C) show a sinogram or projection information values produced when the phantom having a circular section is employed in the first embodiment.

DETAILED DESCRIPTION OF THE INVENTION

Referring to appended drawings, a description will be made of preferred embodiments of a correction coefficient calculating method and a beam-hardening post-processing method for CT systems in accordance with the present invention, and of a CT system to which the methods are adapted.

In the embodiments, an X-ray CT system employing X-rays as a radiation will be adopted as the CT system.

Configuration of an X-Ray CT System

Figure 1:
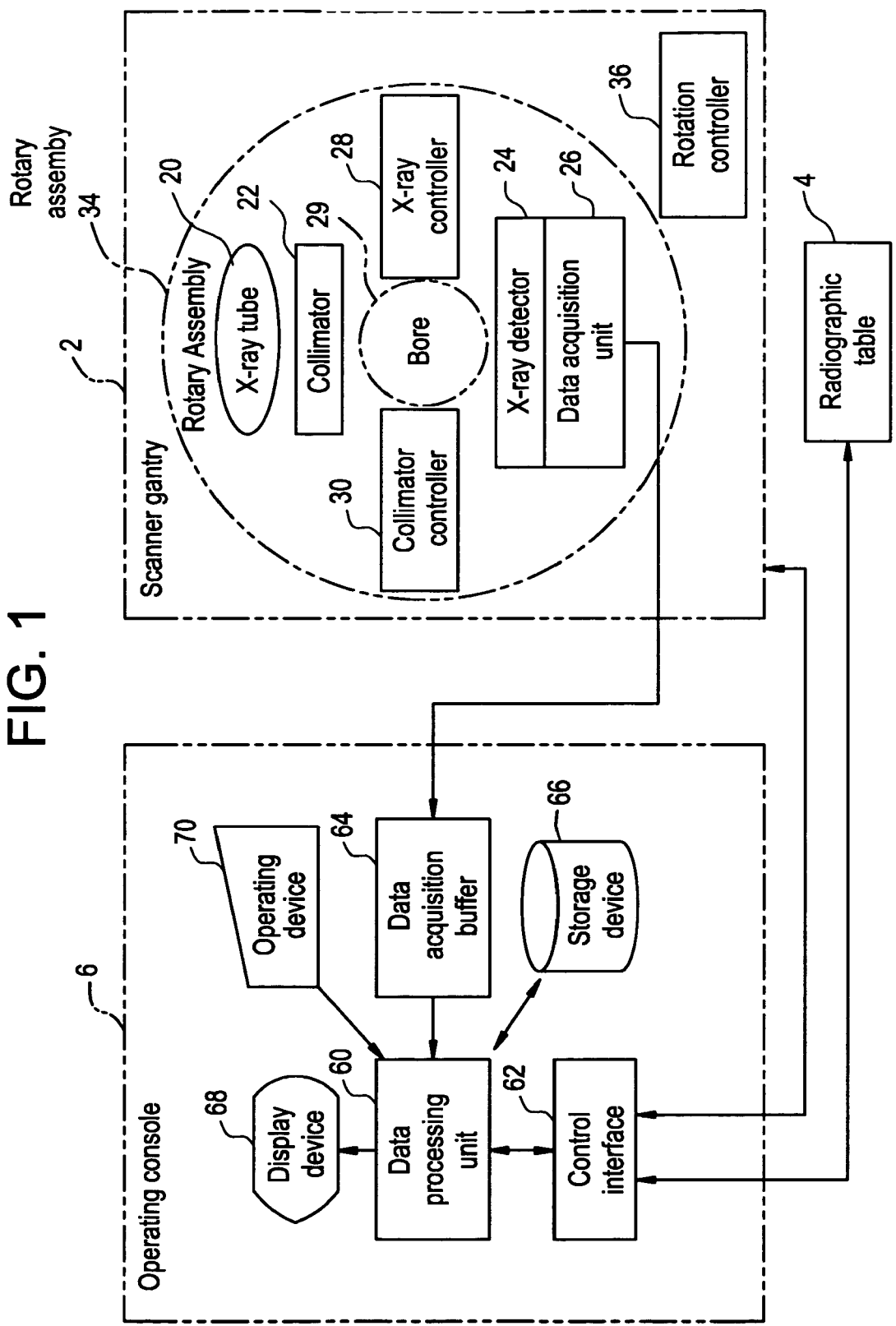
FIG. 1 is a block diagram showing the overall configuration of an X-ray CT system which is one of CT systems and to which a first embodiment of the present invention is adapted.

Referring to FIG. 1, the overall configuration of an X-ray CT system in accordance with the present embodiment will be described below. All embodiments described in this specification are adapted to the X-ray CT system shown in FIG. 1.

The X-ray CT system illustrated in FIG. 1 comprises a scanner gantry 2, a radiographic table 4, and an operating console 6.

Scanner Gantry

The scanner gantry 2 comprises a rotary assembly 34 and a rotation controller 36 that rotates the rotary assembly 34.

Figure 3:
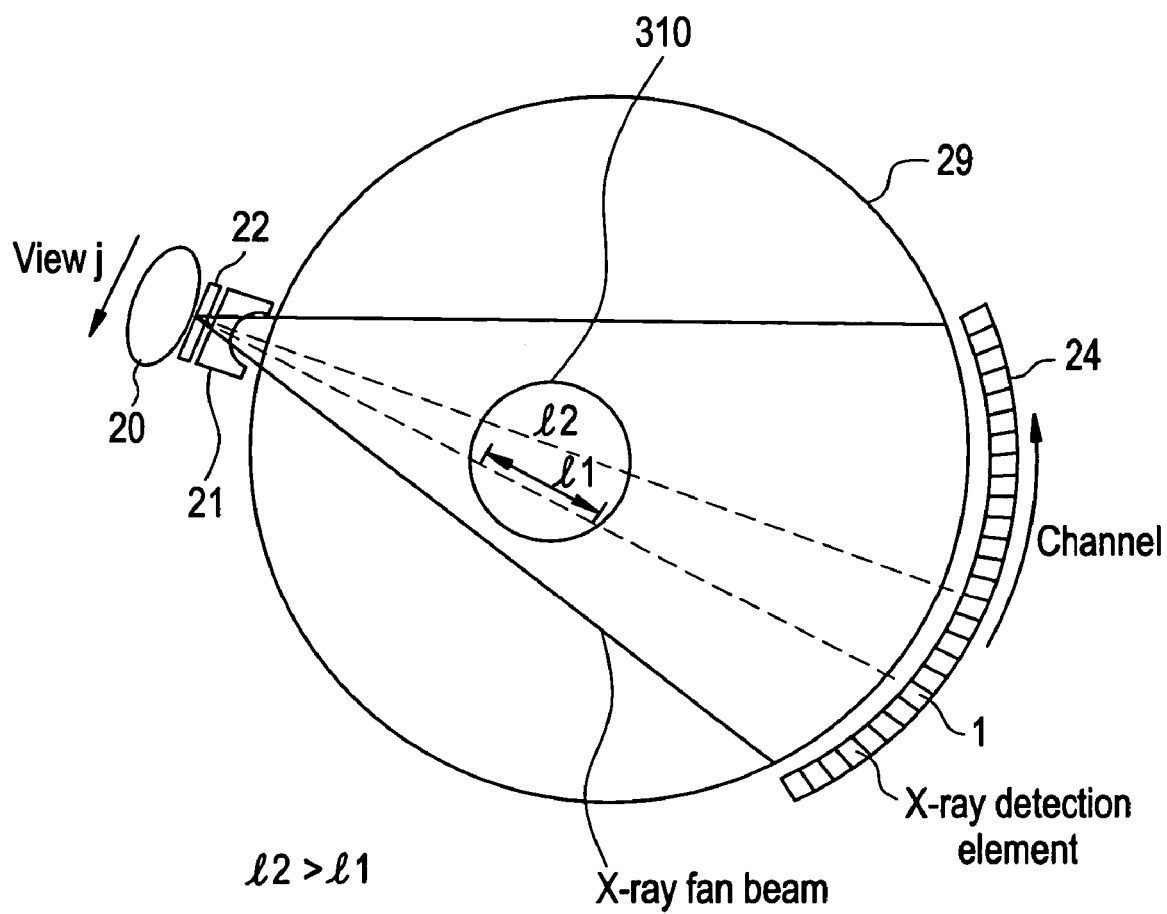
FIG. 3 shows the positional relationship among an X-ray tube, an X-ray detector, and a phantom having a circular section which is established when the phantom having a circular section is employed in the first embodiment adapted to the X-ray CT system illustrated in FIG. 1.

The rotary assembly 34 has, as illustrated with a section thereof enlarged in FIG. 3, an X-ray tube 20 and an X-ray detector 24 opposed to each other with a bore 29 between them. The rotary assembly 34 further comprises a bow-tie filter 21 (not shown in FIG. 1), a collimator 22, a collimator controller 30, an X-ray controller 28, and a data acquisition unit 26.

For examination, a subject lies in the bore 29. For calibration, a phantom 310 having a circular section as shown in FIG. 3 is positioned in the bore 29. The subject or phantom positioned in the bore 29 is placed on a cradle located within the bore 29 in the center of the rotary assembly 34.

The rotary assembly 34 is rotated while being controlled by the rotation controller 36. During the rotation, the X-ray tube 20 irradiates X-rays to the X-ray detector 24. The X-ray detector 24 detects the X-rays transmitted by the subject or phantom. The data acquisition unit 26 acquires the results of the detection performed by the X-ray detector 24. The results of the acquisition are processed as projection information composed of views within the operating console 6.

The X-ray controller 28 controls X-irradiation from the X-ray tube 20. The collimator 22 recomposes X-rays irradiated from the X-ray tube 20 so as to produce, for example, a fan-shaped X-ray beam, that is, fan-beam X-rays. Furthermore, the bow-tie filter 21 regulates the X-rays, which diffuse in the form of a fan, so that the intensities of the X-rays will be evened out over the whole surface of the X-ray detector 24. Eventually, the X-rays fall on the X-ray detector 24 via the bore 29.

The collimator controller 30 controls the collimator 22.

The X-ray detector 24 includes, as illustrated in FIG. 3, a plurality of X-ray detection elements set in array in a direction in which the fan-beam X-rays spread. The X-ray detector 24 is designed as a multi-channel detector having the plurality of X-ray detection elements set in array. The X-ray detection elements form an X-ray incidence surface curved like the cylindrical concave surface as a whole. The X-ray detector 24 is formed using, for example, a combination of a scintillator and a photodiode. For the X-ray detector 24, a semiconductor X-ray detection element that utilizes cadmium telluride (CdTe) or an ion-chamber type X-ray detection element that utilizes xenon gas may be adopted.

The X-ray tube 20, bow-tie filter 21, collimator 22, and X-ray detector 24 constitute an X-ray irradiation/detection unit employed in the present invention.

The data acquisition unit 26 is connected to the X-ray detector 24. The data acquisition unit 26 acquires data items detected by the respective X-ray detection elements constituting the X-ray detector 24.

Operating Console

The operating console 6 comprises a data processing unit 60, a control interface 62, a data acquisition buffer 64, a storage device 66, a display device 68, and an operating device 70.

The data processing unit 60 is realized with, for example, a computer having a great capability to perform arithmetic operations on data. The control interface 62 is connected to the data processing unit 60.

The scanner gantry 2 and radiographic table 4 are connected to the control interface 62. The data processing unit 60 controls the scanner gantry 2 via the control interface 62. Specifically, the data acquisition unit 26, X-ray controller 28, collimator controller 30, and rotation controller 36 included in the scanner gantry 2 are controlled by the data processing unit 60 via the control interface 62.

The data acquisition buffer 64 is connected to the data processing unit 60. The data acquisition unit 26 included in the scanner gantry 2 is connected to the data acquisition buffer 64. Data acquired by the data acquisition unit 26 is transferred to the data processing unit 60 via the data acquisition buffer 64.

The data processing unit 60 reconstructs an image using a transmitted X-ray signal, that is, projection information acquired via the data acquisition buffer 64. The storage device 66 is connected to the data processing unit 60. Projection information held in the data acquisition buffer 64, reconstructed tomographic image information, and programs in which the capabilities of the X-ray CT system in accordance with the present embodiment are implemented are stored in the storage device 66.

The display device 68 and operating device 70 are connected to the data processing unit 60. Tomographic image information and other information sent from the data processing unit 60 are displayed on the display device 68. An operator handles the operating device 70 so as to enter various instructions or information which is duly transferred to the data processing unit 60. The operator uses the display device 68 and operating device 70 to interactively operate the X-ray CT system in accordance with the present embodiment.

Radiographic Table 4

The radiographic table 4 is connected to the data processing unit 60 via the control interface 62. Various switches and an operating tool that are handled in order to operate the X-ray CT system, and a display device on which an X-ray CT image processed in the operating console 6 is displayed are mounted on the radiographic table 4.

Figure 2:
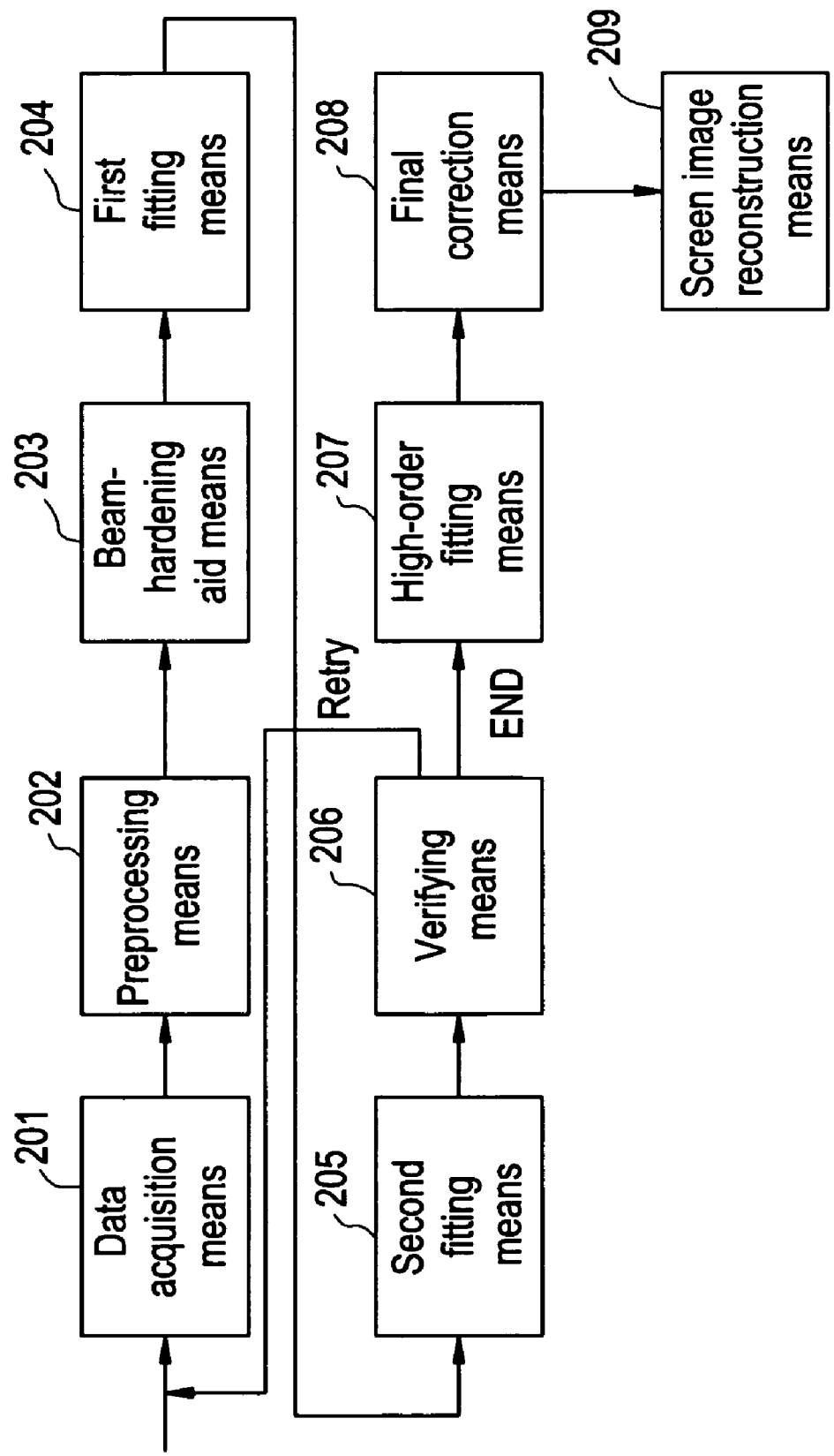
FIG. 2 shows the configuration of a data processing unit included in the X-ray CT system illustrated in FIG. 1.

FIG. 2 is a functional block diagram showing only a portion of the data processing unit 60 relating to a correction coefficient calculating method and a beam-hardening post-processing method in accordance with the present embodiment.

Assuming that the blocks of the data processing unit 60 relating to the present invention are grouped into means, the data processing unit 60 comprises a data acquisition means 201, a preprocessing means 202, a beam-hardening (BH) correction means 203, a first fitting means 204, a second fitting means 205, a verifying means 206, a high-order fitting means 207, a final correction means 208, and an image reconstruction means 209. The beam-hardening correction means 203 calculates a correction coefficient from data preprocessed by the preprocessing means 202, and corrects projection information stored in the storage device 66 using the correction coefficient.

The data acquisition means 201 acquires signals, which are detected from a phantom by the X-ray detector 24, via the data acquisition unit 26, and stores as projection information in the storage device 66.

The preprocessing means 202 performs preprocessing in preparation for correction of projection information in terms of the beam hardening, for example, removes a noise.

The beam-hardening correction means 203 calculates correction coefficients $B_0$ to $B_3$ in relation to each of the channels of the X-ray detector, stores them in the form of a correction coefficient table in the storage device 66, and uses the correction coefficients $B_0$ to $B_3$ to correct projection information, which is stored in the storage device 66, in terms of the beam-hardening effect. Assuming that the projection information value detected on each of the channels of the X-ray detector 24 is Ih and data corrected in terms of the beam-hardening effect is IC, beam-hardening correction is expressed as follows:

$$IC = B_0 \cdot Ih + B_1 \cdot Ih^2 + B_2 \cdot Ih^3 + B_3 \cdot Ih^4 \quad (1)$$

The first fitting means 204 smoothes projection information data items, that is, views that are stored in the storage device 66 and detected on each of the channels of the X-ray detector. A function resulting from the fitting does not reflect high-frequency components of signals that are higher than frequency components determined with the order of the function. The fitting therefore provides the same effect as smoothing.

The second fitting means 205 fits a linear function or higher-degree function close to projection information values which are detected on one of the channels of the X-ray detector 24 and close to which a first function is fitted by the first fitting means 204. This results in a correction coefficient similar to the one provided by the expression (1) employed in the beam-hardening correction means 203.

The verifying means 206 verifies whether the foregoing processing should be performed using different phantoms in order to improve precision in correction.

The high-order fitting means 207 fits a high-order function close to correction coefficients calculated using different phantoms.

The final correction means 208 uses the correction coefficient calculated as mentioned above to finally correct projection information.

The image reconstruction means 209 uses a sinogram, which is produced based on projection information composed of a plurality of views stored in the storage device 66, to reconstruct a tomographic image of a subject or a phantom, for example, a phantom 310 having a circular section as illustrated in FIG. 2. For example, filtered back projection or any other method is adopted for image reconstruction. The reconstructed image is displayed on the display device 68.

First Embodiment

A first embodiment of the present invention will be described on the assumption that the phantom 310 having a circular section is positioned in the bore 29. Herein, the phantom 310 shall be located at a position off the center of the bore 29.

The phantom 310 is made of a material analogous to the composition of a human body that is a subject. For example, the phantom 310 is made of a material such as polypropylene, is shaped like a cylinder, and has a diameter of, for example, 35 cm.

A description will be made of basic actions to be performed by the X-ray CT system in order to acquire data from the phantom 310 located in the bore 29 and to produce projection information and a sinogram.

FIG. 3 shows the phantom 310 having a circular section and being located in the bore 29 of the scanner gantry 2. The phantom 310 has a circular section, and the center of the phantom 310 is located at a position different from the position of the center of the X-ray field in the bore 29.

When X-rays irradiated from the X-ray tube 20 are transmitted by the bow-tie filter 21, their intensities are regulated (smoothed in the direction of the channels of the X-ray detector 24). An X-ray fan beam into which the X-rays are recomposed by the collimator 22 is transmitted by the phantom 310 having a circular section, and detected by the X-ray detector 24.

The X-ray detector 24 has a plurality of X-ray detection elements set in array in the direction in which the X-ray fan beam spreads. The X-ray detector 24 detects projection information concerning the phantom 310 on the channels set in array.

Figure 4:
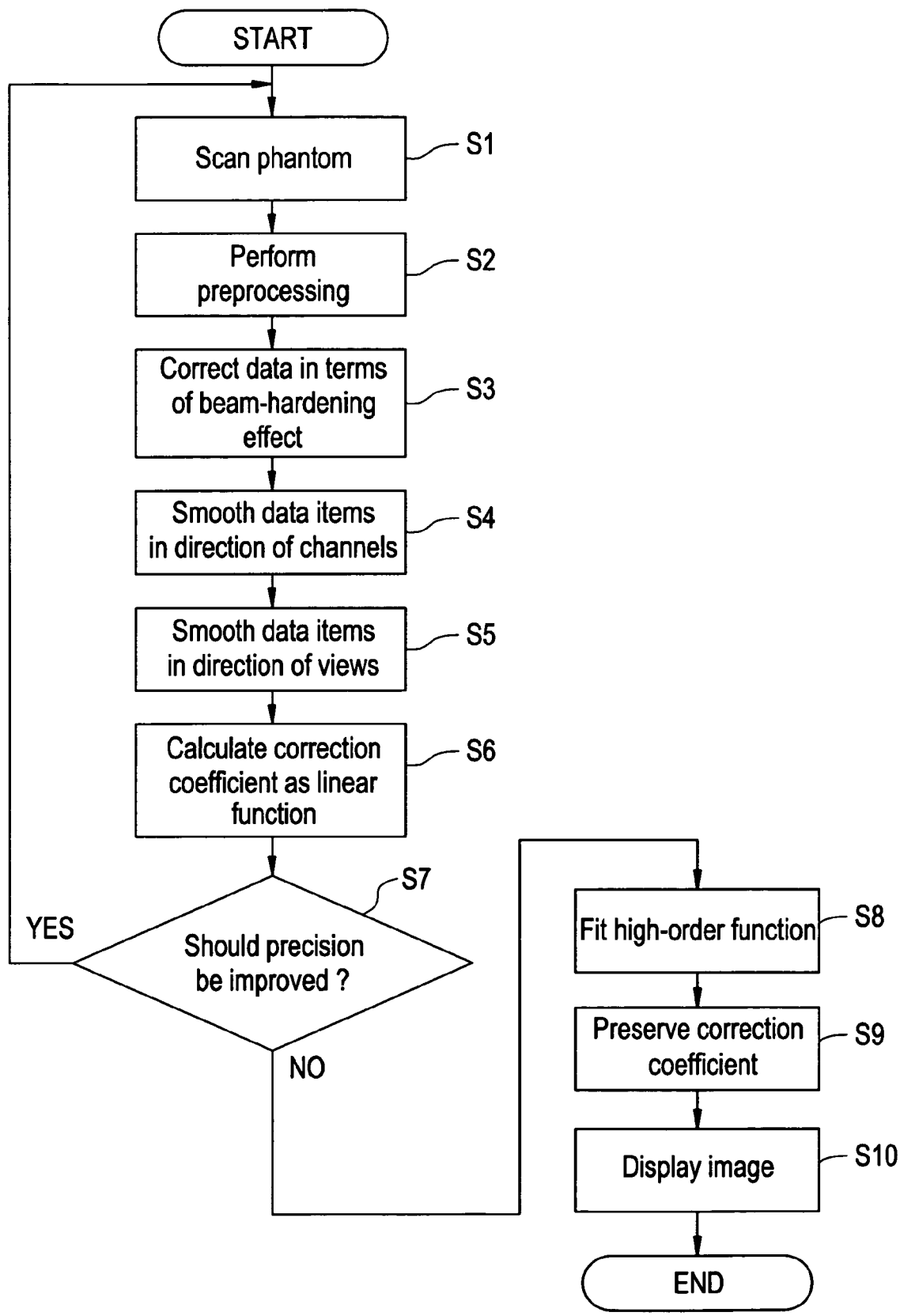
FIG. 4 is a flowchart describing actions to be performed in the data processing unit employed in the first embodiment.

FIG. 4 is a flowchart describing a process that involves the means included in the data processing unit 60.

Step 1: Scanning the Phantom

Step 1 of scanning the phantom is shown as S1 in FIG. 4. First, an operator places the phantom 310 having a circular section at a predetermined position in the bore 29. However, the phantom 310 shall be located at a position off the center of the X-ray field in the bore 29. As mentioned above, the phantom 310 having a circular section shall be made of a material such as polypropylene, be shaped like a cylinder, and have a diameter of, for example, 35 cm.

The data acquisition means 201 included in the data processing unit 60 scans the phantom 310 having a circular section. First projection information 601 resulting from the scan is stored in the storage device 66. Specifically, the X-ray tube 20, collimator 22, and X-ray detector 24 are disposed so that the X-ray tube 20 and collimator 22 will be opposed to the X-ray detector 24 with the bore 29 between them. The rotary assembly 34 including the X-ray tube 20, collimator 22, and X-ray detector 24 is rotated with the bore 29 as a center without a change in the relative positions of the X-ray tube 20, collimator 22, and X-ray detector 24. At this time, the data acquisition means 201 included in the data processing unit 60 acquires projection information via the data acquisition unit 26, and stores the projection information in the storage device 66.

As mentioned above, the data acquisition means 201 included in the data processing unit 60 acquires projection information as a view having a view number associated with each rotation angle, that is, a view angle, produces a sinogram, and stores the sinogram in the storage device 66.

FIG. 5(A) shows an example of a sinogram based on data acquired from the phantom 310 having a circular section. The sinogram comprises a projection information section defined around the center of one dimension of the sinogram associated with channel numbers, and an air data section defined on both sides of the projection information section along the dimension associated with channel numbers. The phantom 310 having a circular section is located off the center of the X-ray field. The channel numbers falling within the channel-direction width of the projection information section vary along with a change in the rotation angle of the rotary assembly 34, that is, a change in the view number. As illustrated in FIG. 5(A), the projection information section is tortuous in the direction of the view numbers. For the same reason, the channel-direction width of the projection information section varies along with a change in the view number.

FIG. 5(B) is a graph whose axis of abscissas indicates channel numbers and whose axis of ordinates indicates projection information values, wherein projection information of view number j indicated in FIG. 5(A) is pointed out. The projection information value is proportional to a length in the phantom 310 having a circular section over which an X-ray beam is transmitted. X-rays passing through near the center of the phantom 310 are transmitted over a large length and provide a large projection information value. X-rays passing through near the periphery of the phantom 310 are transmitted over a small length, provide a small projection information value, and render a semicircular projection image like the one shown in FIG. 5(B).

A projection information value indicated with view number j and channel number i will be taken for instance.

When a view of view number j is acquired, the X-ray beam indicated with dashed lines in FIG. 3 falls on a channel of channel number 1 included in the X-ray detector 24. At this time, a length in the phantom 310 having a circular section over which the X-ray beam is transmitted shall be l. The length l is proportional to a projection information value h detected on the channel i as indicated in FIG. 5(B). In short, l∝h is established.

Referring to FIG. 3, the phantom 310 having a circular section is located at a position off the center of the X-ray field. Therefore, the length l over which X-rays falling on the channel i are transmitted varies depending on a view. The projection information value h detected on the channel i shown in FIG. 5(B) varies depending on a view.

FIG. 5(C) is a graph whose axis of abscissas indicates view numbers and whose axis of ordinates indicates projection information values, wherein a projection information value detected on a channel of channel number i indicated in FIG. 5(A) is pointed out. The projection information value varies depending on the view number, and is proportional to a length in the phantom 310 having a circular section over which an X-ray beam is transmitted. Thus, the projection information value is provided as a function represented with a curve exhibiting cyclicity as shown in FIG. 5(C).

Step 2: Preprocessing

Figure 6:
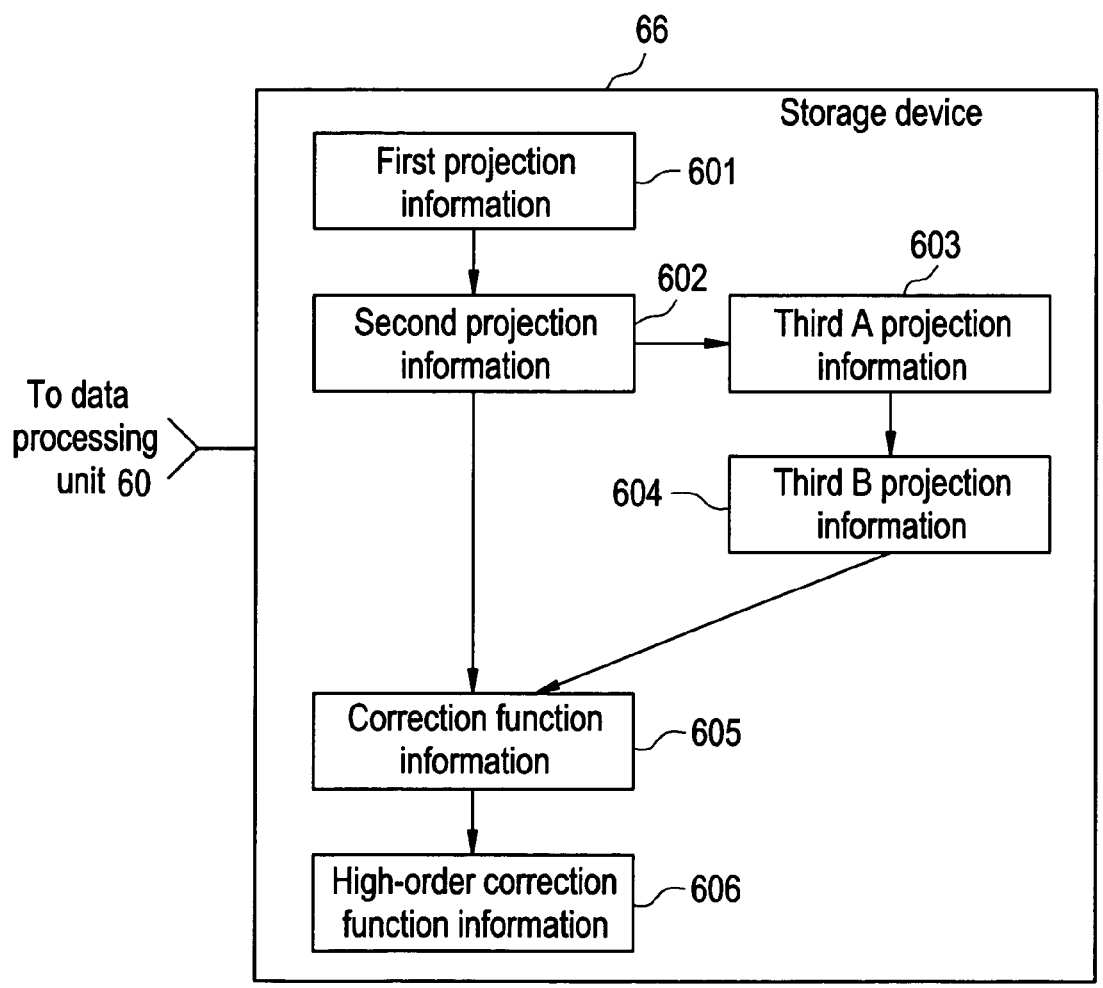
FIG. 6 is a block diagram showing files stored in a storage device employed in the first embodiment as illustrated in FIG. 1.

Step 2 of preprocessing is shown as S2 in FIG. 4. FIG. 6 shows files that are produced during preprocessing, stored in the storage device 66, and have intermediate projection information recorded therein.

Step 3: Correcting Data in Terms of the Beam-Hardening Effect

Figure 7A:
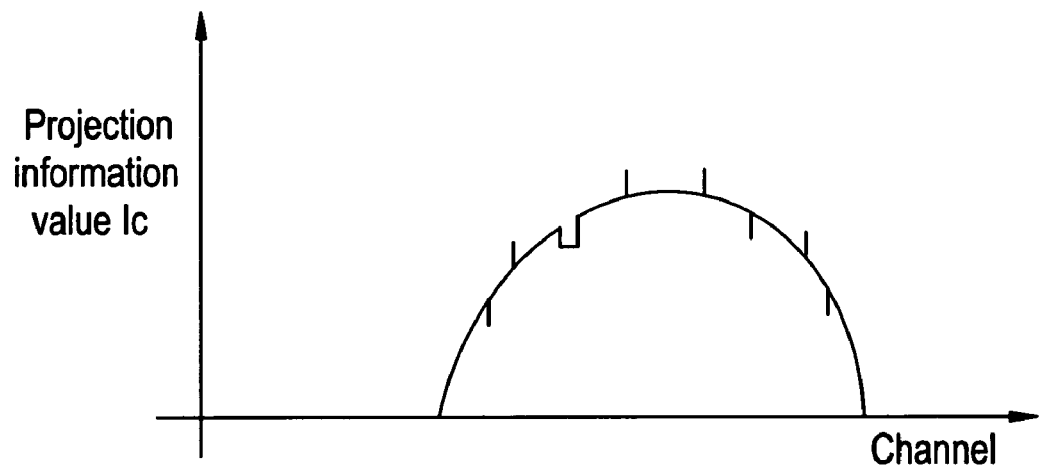
FIG. 7(A) and FIG. 7(B) indicate processing to be performed on projection information values in the direction of channels according to the first embodiment.
Figure 8A:
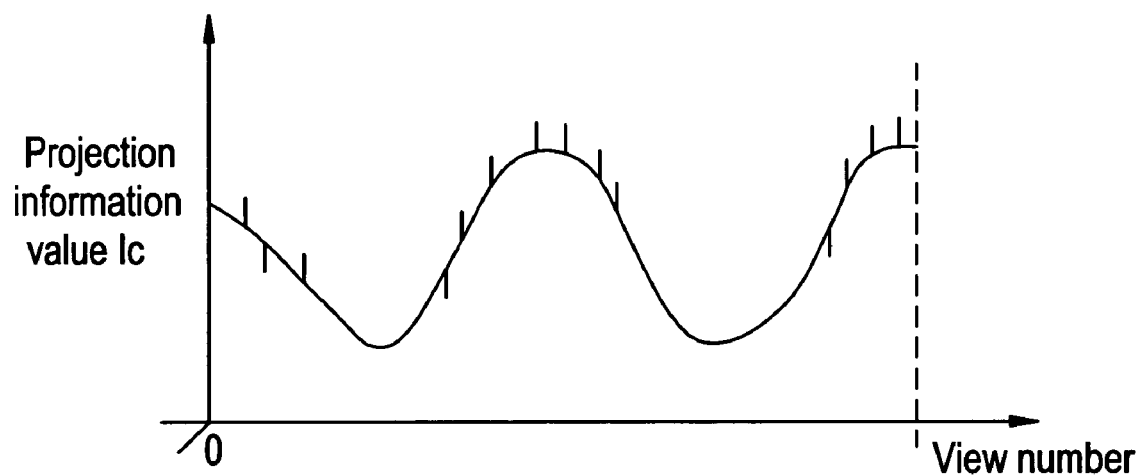
FIG. 8(A) and FIG. 8(B) indicate processing to be performed on projection information values in the direction of views according to the first embodiment.

Step 3 of correcting data in terms of the beam-hardening effect is shown as S3 in FIG. 4. The beam-hardening correction means 203 included in the data processing unit 60 corrects projection information values Ih in terms of the beam-hardening effect using the expression (1), and thus calculates corrected projection information values Ic. The results of the correction are stored as second projection information shown in FIG. 6 in the storage device 66. The file has the beam-hardening effect generally removed therefrom. However, the beam-hardening effect slightly remains because of a difference of each channel of the X-ray detector 24 from the others. FIG. 7(A) illustratively shows an example of the second projection information. The second projection information is plotted as a semicircular curve because it is produced from projection information acquired from a generally circular phantom. However, the projection information values Ic sampled in relation to some channels are plotted as pulse-like fluctuations because of a difference in the sensitivity of each channel to X-rays from the other channels. This is a channel-specific phenomenon and must therefore be corrected channel by channel. FIG. 8(A) illustratively shows an example of projection information values sampled from the second projection information in relation to one channel in the direction of views. The projection information values Ic sampled in relation to some views are plotted as pulse-like fluctuations.

Step 4: Smoothing in the Direction of Channels

Step 4 of smoothing in the direction of channels is shown as S4 in FIG. 4. The first fitting means 204 included in the data processing unit 60 smoothes second projection information 602 in the direction of channels. The results of the smoothing are stored as third A projection information 603 shown in FIG. 6 in the storage device 66. The projection information has projection information values Ic thereof, which are plotted as pulse-like fluctuations attributable to a difference of one channel from the other channels, smoothed and removed.

Figure 7B:
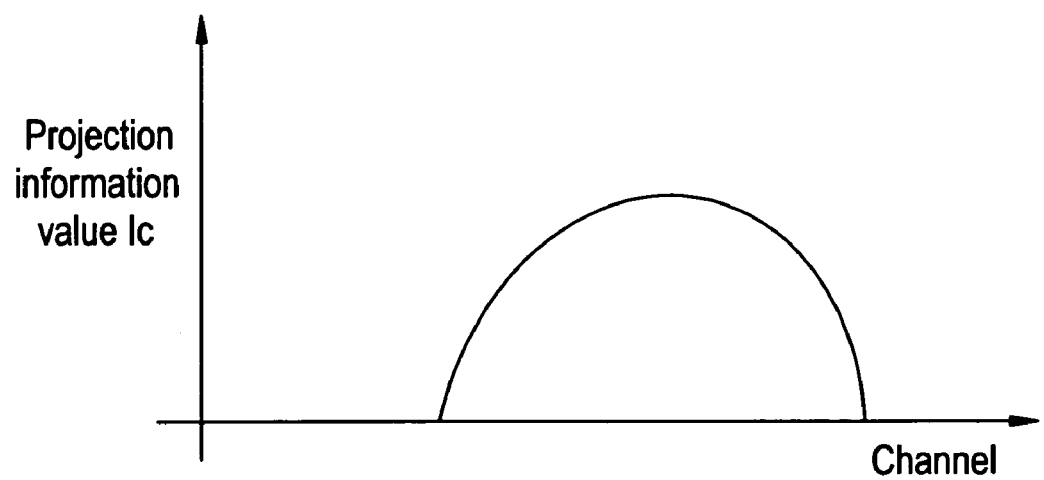

FIG. 7(B) illustratively shows an example of the third A projection information. Projection information is plotted semi-circularly like typical projection information acquired from a circular phantom.

Step 5: Smoothing in the Direction of Views

Figure 8B:
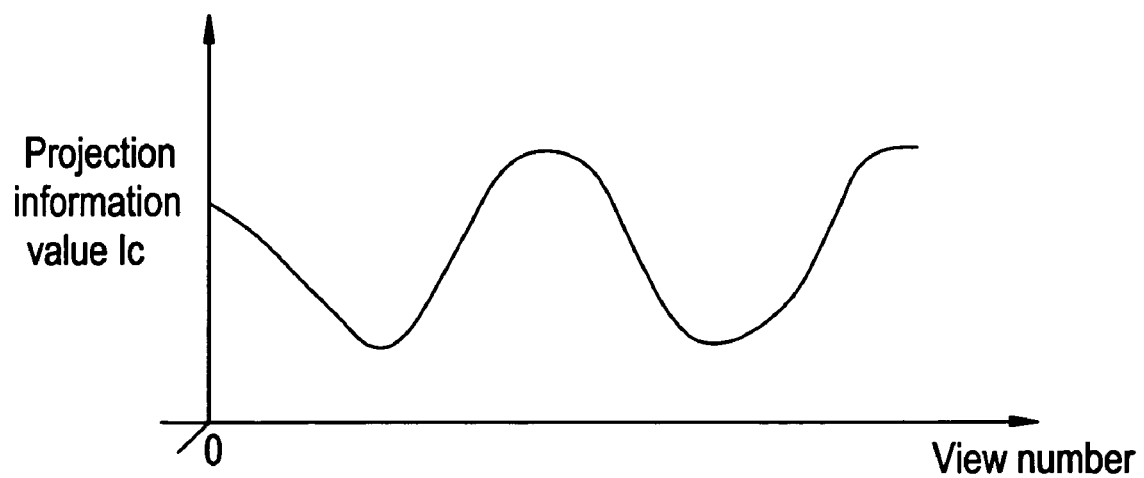

Step 5 of smoothing in the direction of views is shown as S5 in FIG. 4. The first fitting means 204 included in the data processing unit 60 smoothes projection information 603 in the direction of views. Consequently, third B projection information 604 shown in FIG. 6 is produced. The projection information has projection information values, which are plotted as pulse-like fluctuations derived from a difference of one view from the others detected on each channel, smoothed. FIG. 8(B) illustratively shows an example of the third B projection information. The projection information values that are sampled in relation to one channel in the direction of views and that exhibit cyclicity are smoothed.

Step 6: Calculating a Correction Coefficient as a Linear Function

Step 6 of calculating a correction coefficient as a linear function is shown as S6 in FIG. 4. The second fitting means 205 included in the data processing unit 60 calculates a correction coefficient as a linear function from the second projection information and third B projection information. Assume that projection information values sampled from the second projection information in relation to channel number i shall be S(j) and projection information values sampled from the third B projection information in relation to channel number i shall be F(j).

Figure 9A:
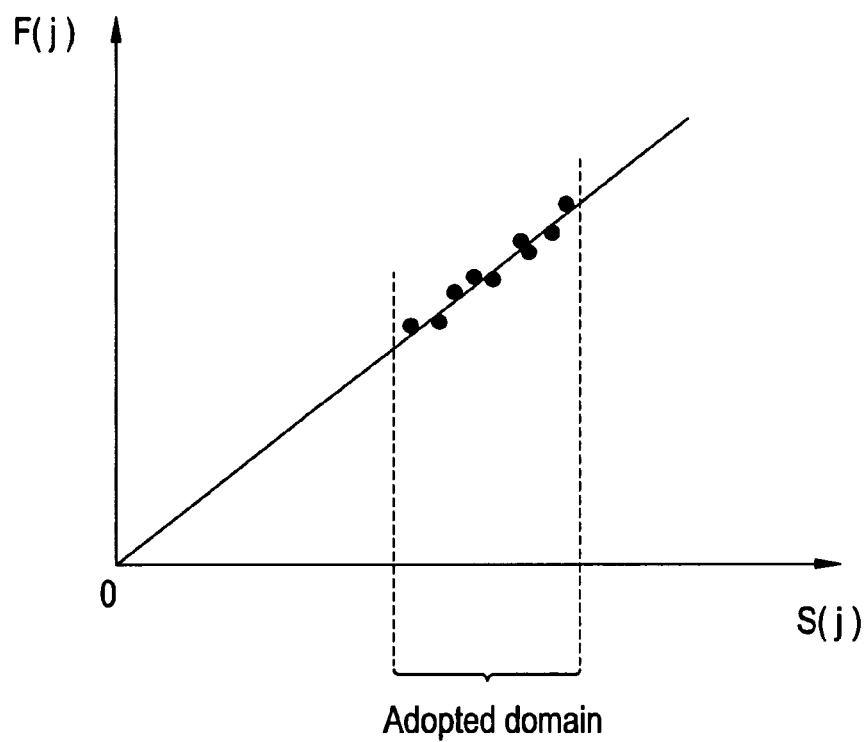
FIG. 9(A) and FIG. 9(B) indicate a correction coefficient calculated from correct projection information values according to the first embodiment.

Projection information values sampled in relation to all respective views assigned view numbers are plotted in FIG. 9(A), wherein the axis of abscissas indicates the second projection information values S(j) and the axis of ordinates indicates the third B projection information values F(j). The projection information values are plotted along a straight line that passes an origin. The straight line represents a linear function expressing a correction coefficient for data values detected on the channel i.

FIG. 9(A) is a graph indicating the relationship between second projection information values S(j) and third B projection information values F(j) which are produced by scanning one phantom.

The correction coefficient is preserved as correction coefficient information 605 in the storage device 66. Assuming that the straight line expressing the correction coefficient has a slope Ki, the slope Ki is expressed as follows:

$$F(j)/S(j) \approx Ki$$

Projection information values Ic produced by correcting projection information, which is acquired from a subject and detected on the channel i, in terms of the beam-hardening effect are multiplied by a correction coefficient Ki as follows:

$$Ip = Ic * Ki$$

Consequently, projection information values Ip are calculated as the results of smoothing or correction performed on projection information acquired from a subject.

The projection information value is proportional to a length l in the phantom 310 having a circuit section as shown in FIG. 3 over which X-rays are transmitted. Therefore, an adopted domain of projection information values S(j) depends on the diameter of the phantom 310 having a circular section and the position of the phantom within the bore 29.

Step 7: Verifying Whether Precision Should be Improved

Step 7 of verifying whether precision should be improved is shown as S7 in FIG. 4. The verifying means 206 included in the data processing unit 60 verifies whether the precision in a correction coefficient should be improved. If the precision in a correction coefficient should be improved, an operator places a phantom, which has a circular section and a different diameter, at a different position off the center of the X-ray field within the bore 29. Steps 1 to 6 are resumed in order to calculate a new correction coefficient using the new phantom.

Figure 9B:
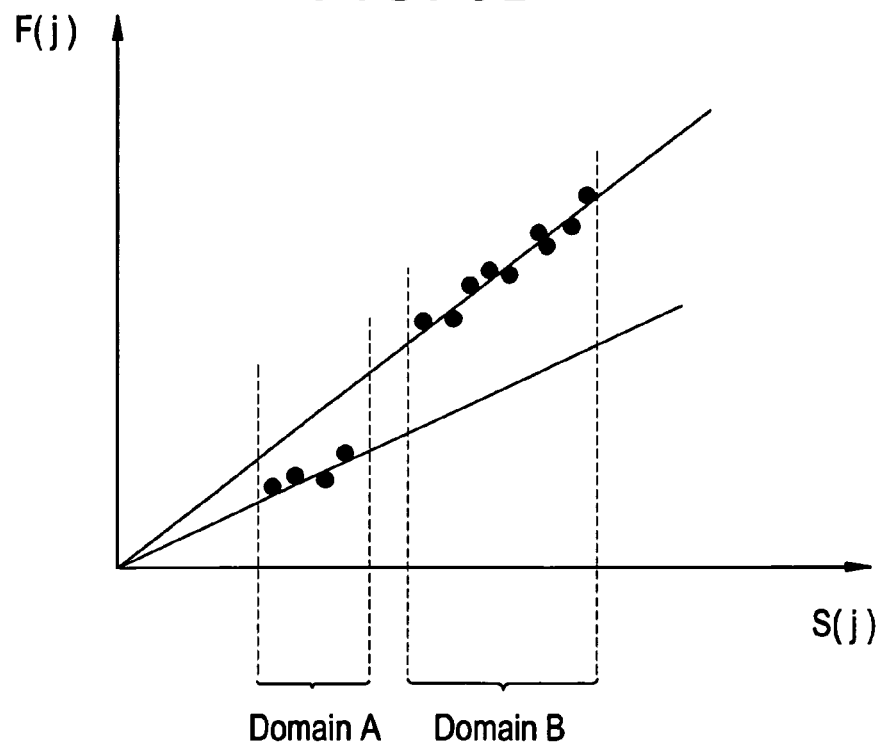

FIG. 9(B) shows an example of correction coefficients obtained using two phantoms whose circular sections have different diameters. A length in the phantom over which an X-ray beam is transmitted is determined with the diameter and position of the phantom. Projection information values S(j) are also determined. Consequently, assuming that the diameters of the phantoms whose sections are circular are A and B respectively and the relationship of A<B is established, projection information values acquired from phantom A belong to domain A, and projection information values acquired from phantom B belong to domain B. The beam-hardening correction means 203 calculates correction coefficients from the projection information values belonging to the respective domains.

Step 8: Fitting a High-Order Function

Figure 10:
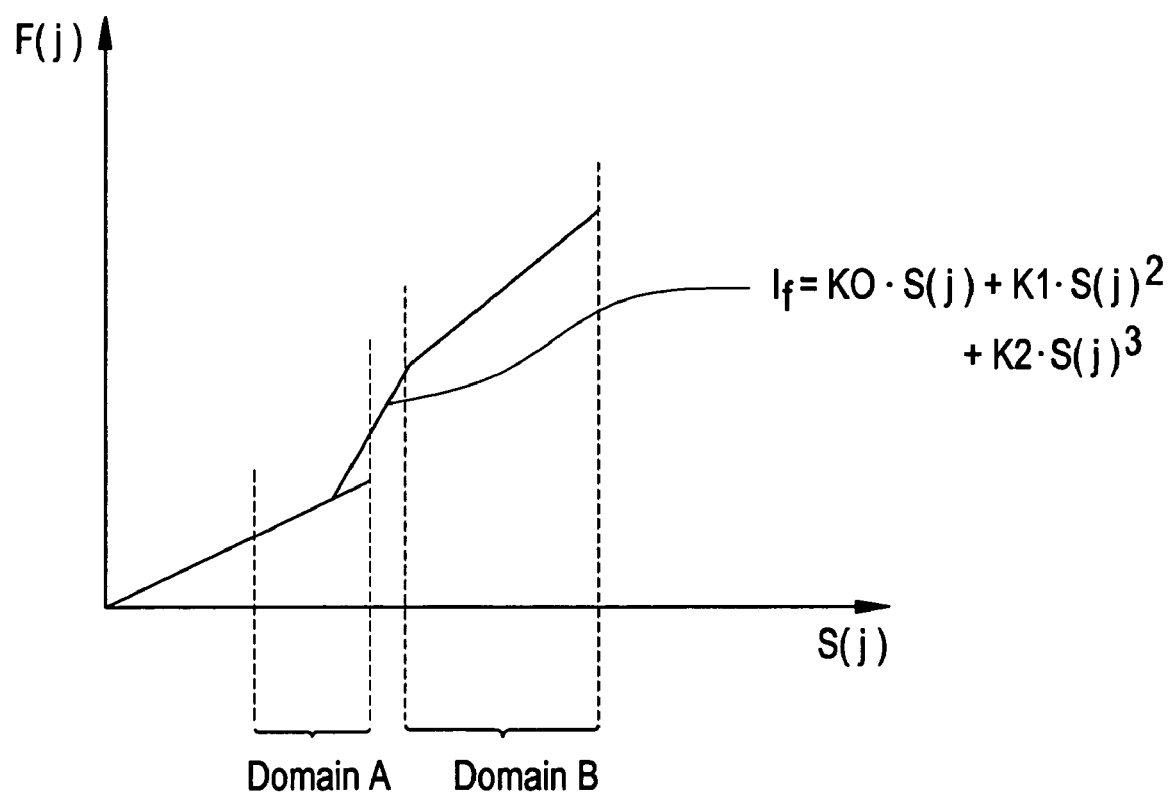
FIG. 10 indicates a second function which is fitted to projection information values according to the first embodiment.

Step 8 of fitting a high-order function is shown as S8 in FIG. 4. A plurality of phantoms is used to perform the foregoing processing. If correction coefficient data acquired is precise enough be accepted, the high-order fitting means 207 included in the data processing unit 60 fits a high-order function close to the correction coefficients that are calculated from the adopted domains. FIG. 10 shows an example of fitting to the correction coefficients obtained using phantoms A and B and indicated in FIG. 9(B). The high-order fitting means 207 fits a third-order function close to the correction coefficient value A calculated from domain A and the correction coefficient value B calculated from domain B, and then determines correction coefficients K0, K1, and K2.

$$If = K0*S(j) + K1*S(j)^2 + K2*S(j)^3 \quad (2)$$

In this case, the correction coefficient calculated from the domain A of small projection information values is thought to be more precise than the correction coefficient calculated from the domain B of large projection information values. The high-order fitting means 207 therefore may apply different weights to the respective domains so that the third function given as the expression (2) will be more precisely fitted to the correction coefficient calculated from the domain A. The correction coefficients in the expression (2) may then be determined.

Step 9: Preserving Correction Coefficients

Step S9 of preserving correction coefficients is shown as S9 in FIG. 4. The high-order fitting means 207 included in the data processing unit 60 preserves high-order correction coefficient information 606 composed of the correction coefficients K0, K1, and K2 in the storage device 66, and terminates the process.

Step 10: Displaying Information

Step S10 of displaying information is shown as S10 in FIG. 4. In order to visualize a subject, the final correction means 208 included in the data processing unit 60 uses the correction coefficients K0, K1, and K2, which are calculated in relation to each channel, to correct projection information values Ic that are acquired from a subject and corrected in terms of the beam-hardening effect. Consequently, projection information values If are calculated according to the expression (2).

The image reconstruction means 209 reconstructs an image using the projection information values If so as to produce tomographic image information, and displays the image on the display device 68 and/or the display unit of the radiographic table 4.

As mentioned above, according to the first embodiment, phantoms whose circular sections have different diameters are placed at positions off the center of the X-ray field. A length in the phantoms over which an X-ray beam is transmitted is different from view to view. Projection information whose values are different from view to view is detected on each channel. After the projection information values are corrected in terms of the beam-hardening effect, the projection information values are corrected in relation to each channel. Correction coefficients are approximated using a high-order function. Consequently, correction can be achieved in consideration of a non-linear effect attributable to the beam-hardening effect. The high-precision correction coefficients can be calculated using a small number of phantoms. Therefore, a temporal load and physical load an operator has to incur for the purpose of calibration can be alleviated.

The foregoing method includes fitting of a third-order function given as the expression (2). Alternatively, fitting of a second-order or fourth or higher-order function will do.

According to the present embodiment, as described at step 6 in FIG. 4, a sinogram is used to calculate a correction coefficient as a linear function. Alternatively, a sinogram may be used to calculate second projection information 602 and third projection information 604, and a high-order function may be fitted to the second projection information 602 and third projection information 604. Thus, correction coefficients provided as a high-order function may be calculated but a correction coefficient provided as a linear function may not.

According to the first embodiment of the present invention, one or a plurality of phantoms whose circular sections have different diameters is placed at positions off the center of the X-ray field, and scanned in order to acquire first projection information composed of all views. One or a plurality of sinograms is produced using the first projection information. The beam-hardening correction means corrects the first projection information in terms of the beam-hardening effect so as to produce second projection information. The first fitting means fits a first function to the second projection information so as to produce third projection information. The second fitting means fits a second function to third projection information values so as to calculate a correction coefficient. Herein, the third projection information values are provided as functions having as respective independent variables second projection information values that are sampled in relation to all the views and each of the channels. The correction means uses the correction coefficient to correct projection information acquired from a subject who lies in the scan field. The second projection information values vary depending on the view or sinogram. Therefore, when the correction coefficient is calculated through fitting of a function, a large domain of second projection information values is used to calculate a correction coefficient, and fitting of functions is performed. This leads to the improved precision in a correction coefficient, whereby image quality can be improved. Otherwise, a small number of phantoms may be used to calculate high-precision correction coefficients. In this case, correction coefficients can be calculated easily.

Assessment of First Embodiment

In the first embodiment that employs the phantom 310 having a circular section, a length in the phantom 310 having a circular section over which X-rays are transmitted varies depending on a direction. Therefore, the intensity of transmitted X-rays that reach the X-ray detector 24 is not uniform. For example, referring to FIG. 3, a length 11 over which X-rays are transmitted is smaller than a length 12 over which X-rays are transmitted.

On the other hand, the sections of the trunk and head of a human body are shaped like a rounded ellipse.

Even in the first embodiment, the bow-tie filter 21 is used to regulate X-rays irradiated from the X-ray tube 20 so that the intensity of X-rays incident on the X-ray detector 24 will become uniform. This is intended to prevent detection of incorrect data even if a distance in the phantom 310 having a circular section over which X-rays are transmitted varies. However, in order to improve precision in correction, various kinds of bow-tie filters 21 are needed so that an optimal one of the bow-tie filters can be adopted for calibration.

As described in relation to the first embodiment, a plurality of cylindrical phantoms having different diameters that generally catch a field of view (FOV) in the center of an X-ray field is scanned. Projection information acquired from the phantoms is used to precisely correct a correction coefficient.

According to the method in accordance with the first embodiment, a work time and operator's labor increase. It is therefore important how a beam-hardening post-processing method and an X-ray CT system are realized in order to readily and highly precisely correct projection data in terms of the beam-hardening effect in relation to each channel while taking account of a non-linear effect. The second and subsequent embodiments provide methods for overcoming the above drawback of the first embodiment.

Second Embodiment

Figure 11:
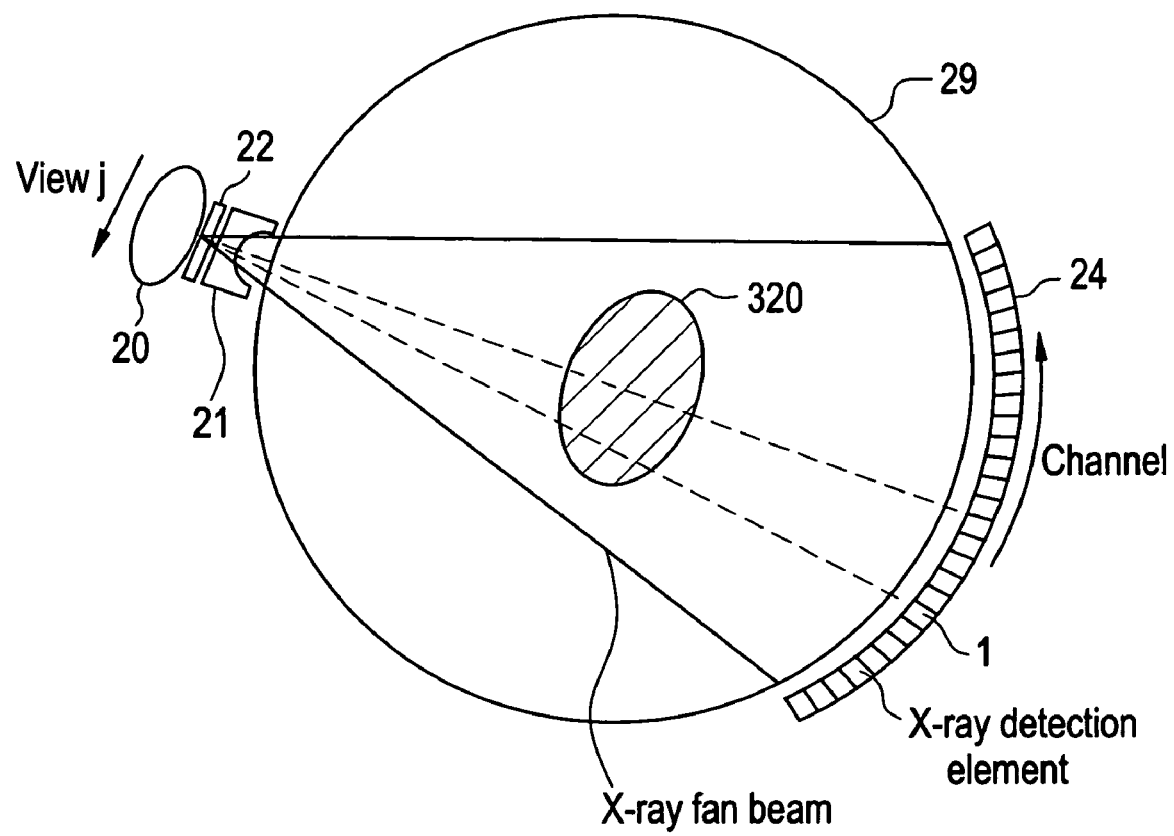
FIG. 11 shows the positional relationship among the X-ray tube, and the X-ray detector, and a phantom having a circular section which is established when a second embodiment employing the phantom having an oblong section is adapted to the X-ray CT system illustrated in FIG. 1.

In a second embodiment, as illustrated in FIG. 11, a phantom 320 having an oblong section is disposed in the scan field within the bore 29 between the X-ray tube 20 and X-ray detector 24. A method of correcting projection data acquired from the phantom 320 having an oblong section in terms of the beam-hardening effect, and calculating a correction coefficient will be described below. FIG. 11 is equivalent to FIG. 3 showing the first embodiment.

The oblong section of the phantom 320 resembles the section of the trunk of a human body. The phantom 320 is made of the same material as the phantom 310 having a circular section and being described in relation to the first embodiment.

A difference of the second embodiment from the first embodiment lies in that the phantom 310 having a circular section is replaced with the phantom 320 having an oblong section.

An X-ray CT system to which the second embodiment is adapted is identical to the one illustrated in FIG. 1. Therefore, iterating the X-ray CT system with reference to FIG. 1 will be omitted.

Even in the second embodiment, the data processing unit 60 has the same configuration as the one employed in the first embodiment and described with reference to FIG. 2. Namely, the data processing unit 60 comprises the data acquisition means 201, preprocessing means 202, beam-hardening correction means 203, first fitting means 204, second fitting means 205, verifying means 206, high-order fitting means 207, final correction means 208, and operator image reconstruction means 209.

Calibrating Method

Except that the phantom is replaced with the phantom 320 having an oblong section, a process involving the means included in the data processing unit 60 illustrated in FIG. 2 is identical to the one employed in the first embodiment and described with reference to FIG. 4. The process will be outlined below.

Step 1 An operator places the phantom 320 having an oblong section on a central line linking the centers of the X-ray tube 20 and X-ray detector 24 in the center of the X-ray field in the scan field in which a subject is positioned. Incidentally, the phantom 320 having an oblong section is disposed so that it will be fully exposed to X-rays spreading in the form of a fan from the X-ray tube 20 to the X-ray detector 24. At this time, X-rays that do not pass the phantom 320 having an oblong section must be detected at the edge of the X-ray detector 24.

The data acquisition means 201 included in the data processing unit 60 acquires first projection information from the phantom 320 having an oblong section after the phantom 320 is scanned in multiple directions in order to acquire a plurality of views. The data acquisition means 201 then produces one sinogram.

The features (profile) of projection information calculated by the data acquisition means 201 are different from those represented as FIG. 5(A) to FIG. 5(C) and acquired from the phantom 310 having a circular section. The projection information acquired from the phantom 320 having an oblong section is unique to the phantom 320.

Step 2 If necessary, the preprocessing means 202 included in the data processing unit 60 performs the same preprocessing on first projection information as that employed in the first embodiment.

Step 3 The beam-hardening correction means 203 included in the data processing unit 60 corrects, similarly to the one employed in the first embodiment, the preprocessed first projection information in terms of the beam-hardening effect so as to produce second projection information. The values assigned to the coefficients $B_0$ to $B_3$ in the expression (1) are different from those employed in the first embodiment. However, the same correction expression is employed.

Steps 4 and 5 The first fitting means 204 included in the data processing unit 60 smoothes, similarly to the one employed in the first embodiment, projection information values in the direction of channels and in the directions of views.

Step 6 The second fitting means 205 included in the data processing unit 60 calculates, similarly to the one employed in the first embodiment, a correction coefficient as a linear function.

Figure 12A:
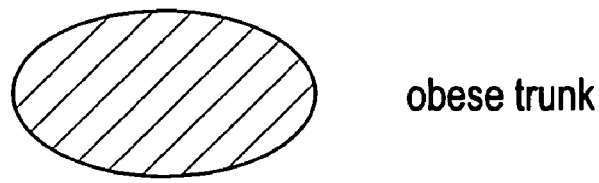
FIG. 12(A) and FIG. 12(B) are sectional views of various phantoms having oblong sections and being employed in the second embodiment.
Figure 12B:
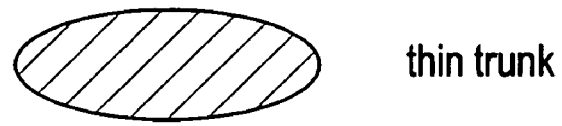
Figure 13A:
FIG. 13(A) to FIG. 13(C) are sectional views of various phantoms having oblong sections and being employed in the second embodiment.
Figure 13B:
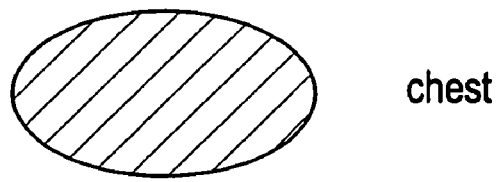
Figure 13C:
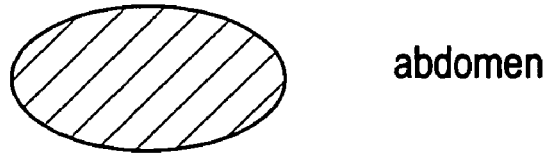

Step 7 If necessary, an operator instructs whether the foregoing process should be repeatedly performed on a plurality of phantoms having oblong sections that are, as shown in FIG. 12(A) and FIG. 12(B), different from each other in ellipticity or on a plurality of phantoms having oblong sections that are, as shown in FIG. 13(A) to FIG. 13(C), different from one another in dimension, shape, or material. The verifying means 206 verifies whether such a request is issued.

As the phantom 320 having an oblong section, a plurality of phantoms whose shapes resemble the shapes of regions to be diagnosed using the X-ray CT system or the shapes of subjects' bodies can be adopted.

Step 8 After the foregoing process is executed for a plurality of phantoms having oblong sections, the high-order fitting means 207 included in the data processing unit 60 fits a high-order function to a set of correction coefficients so as to calculate final correction coefficients.

Step 9 The final correction means 208 uses the final correction coefficients to correct projection information.

Step 10 The image reconstruction means 209 included in the data processing unit 60 re-calibrates a corrected image and displays it on the display device 68.

The shape of the phantom 320 having an oblong section and being employed in the second embodiment resembles the shape of the trunk or head of a human body that is a subject. Using the phantom 320, a more accurate correction coefficient can be calculated than the one calculated using the phantom 310 having a circular section and being employed in the first embodiment.

Various phantoms having oblong sections like the ones shown in FIG. 12(A) and FIG. 12(B) and FIG. 13(A) to FIG. 13(C) are used to calculate respective correction coefficients. Therefore, correction coefficients adaptable to various subjects of various conditions, for example, an adult, a child, a female, a male, an obese person, and a slim person, or the head, chest, trunk, or leg of the same subject can be calculated.

Variant

According to the aforesaid embodiments, the aforesaid process is repeatedly performed on various phantoms. Based on the results, at step 8, the high-order fitting means 207 fits a higher-order function to correction coefficients. Alternatively, individual correction coefficients may be calculated in relation to the shapes or materials of phantoms having oblong sections, and preserved in the storage device 66.

The X-ray CT system may be used to correct projection information according to the subject's region to be examined, for example, the head, chest, trunk, or leg. Similarly, a correction coefficient can be selected for use depending on whether the chest or trunk to be examined is the check or trunk of a large subject, an obese subject, or the like. Moreover, a correction coefficient may be selected for use depending on whether the subject is a child or an adult.

Third Embodiment

Figure 14:
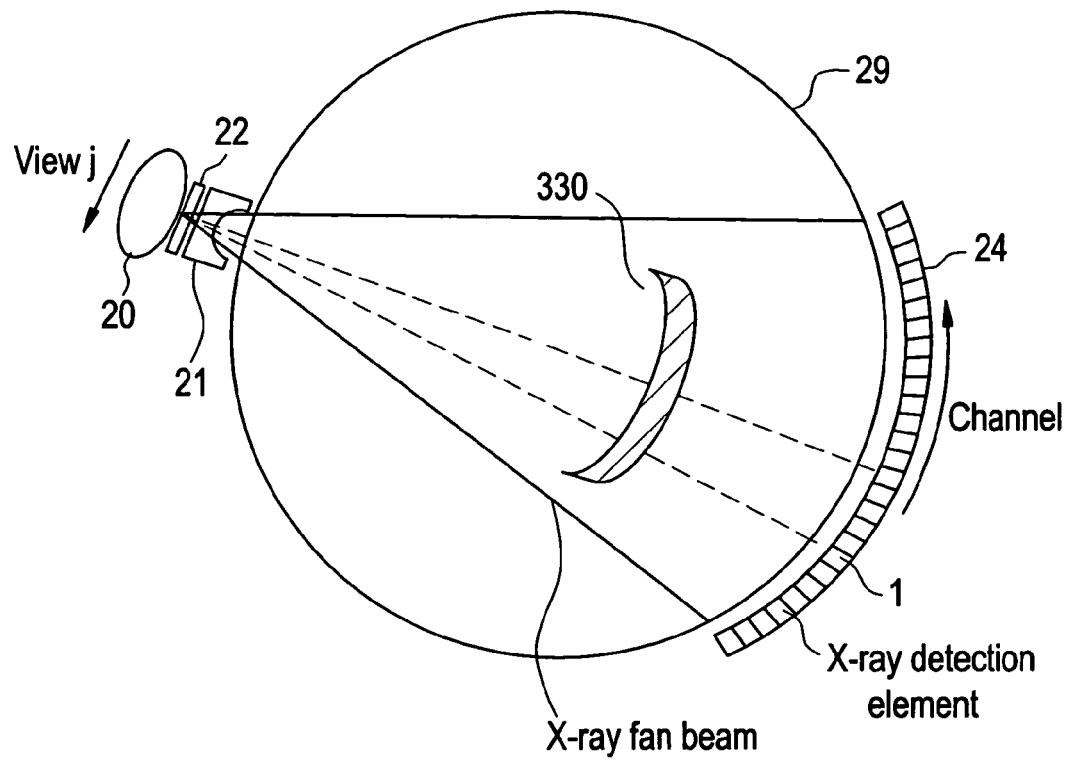
FIG. 14 shows the positional relationship among the X-ray tube, the X-ray detector, and a phantom having a circular section which is established when a third embodiment that employs a phantom having an annular (sector) section and a uniform thickness is adapted to the X-ray CT system illustrated in FIG. 1.

As a third embodiment, a method of calculating a correction coefficient will be described below. As illustrated in FIG. 14, a phantom 330 having a annular (sector) section and a uniform thickness is placed in the scan field within the bore 29 between the X-ray tube 20 and X-ray detector 24. Projection information acquired from the phantom 330 is corrected in terms of the beam-hardening effect in order to calculate a correction coefficient. FIG. 14 is equivalent to FIG. 3 showing the first embodiment.

The material of the phantom 330 having a annular (sector) section and a uniform thickness is the same as the one of the phantom 310 having a circular section and being described in relation to the first embodiment.

A difference between the first and second embodiments lies in that the phantom 310 having a circular section is replaced with the phantom 330 having an annular (sector) section and a uniform thickness.

The third embodiment is adapted to an X-ray CT system identical to the one illustrated in FIG. 1. Therefore, describing the X-ray CT system with reference to FIG. 1 will be omitted.

Even in the third embodiment, the data processing unit 60 has the same configuration as the one employed in the first embodiment and described with reference to FIG. 2. Namely, the data processing unit 60 comprises the data acquisition means 201, preprocessing means 202, beam-hardening correction means 203, first fitting means 204, second fitting means 205, verifying means 206, high-order fitting means 207, final correction means 208, and operator image reconstruction means 209.

Calibrating Method

Except that the phantom 310 having a circular section is replaced with the phantom 330 having an oblong section, the process involving the means included in the data processing unit 60 illustrated in FIG. 2 is identical to the one employed in the first embodiment and described with reference to FIG. 4. The outline is identical to the one described in relation to the second embodiment.

Step 1 An operator places the phantom 330, which has an annular (sector) section and a uniform thickness, on the central line linking the center of the X-ray tube 20 and the center of the X-ray detector 24 in the center of the X-ray field in the scan field in which a subject is positioned. The phantom 330 is disposed so that it will be fully exposed to X-rays spreading in the form of a fan from the X-ray tube 20 to the X-ray detector 24 and X-rays not transmitted by the phantom 330 will be detected at the edge of the X-ray detector 24.

The data acquisition means 201 included in the data processing unit 60 acquires first projection information from the phantom 330 after the phantom 330 is scanned in multiple directions in order to acquire multiple views, and then produces one sinogram.

The features (profile) of projection information, which is acquired from the phantom 330 having an annular (sector) section and a uniform thickness, calculated by the data acquisition means 201 are different from those of projection information, which is acquired from the phantom 310 having a circular section, represented by FIG. 5(A) to FIG. 5(C). The features of projection information acquired from the phantom 330 having an annular (sector) section and a uniform thickness are unique to the phantom 330.

Step 2 If necessary, the preprocessing means 202 included in the data processing unit 60 performs the same preprocessing on first projection information as the one employed in the first embodiment.

Step 3 The beam-hardening correction means 203 included in the data processing unit 60 corrects, similarly to the one employed in the first embodiment, the preprocessed first projection information in terms of the beam-hardening effect so as to produce second projection information. The values assigned to the coefficients $B_0$ to $B_3$ in the expression (1) are different from those employed in the first embodiment. However, the correction expression is the same.

Steps 4 and 5 The first fitting means 204 included in the data processing unit 60 smoothes, similarly to the one employed in the first embodiment, projection information values in the direction of channels and in the direction of views.

Step 6 The second fitting means 205 included in the data processing unit 60 calculates, similarly to the one employed in the first embodiment, a correction coefficient as a linear function.

Figure 15A:
FIG. 15(A) to FIG. 15(C) are sectional views of various phantoms having annular (sector) sections and uniform thicknesses and being employed in the third embodiment.
Figure 15B:
Figure 15C:

Step 7 If necessary, an operator instructs whether the foregoing process should be repeatedly performed on a plurality of phantoms having oblong sections and being, as shown in FIG. 15(A) to FIG. 15(C), different from one another in thickness, dimension, or orientation. The verifying means 206 verifies whether such a request is issued.

Step 8 After the foregoing process is completed for the plurality of phantoms 330 having an annular (sector) section and a uniform thickness, the high-order fitting means 207 included in the data processing unit 60 fits a high-order function to a set of correction coefficients so as to calculate final correction coefficients.

Step 9 The final correction means 208 uses the final correction coefficients to correct projection information.

Step 10 The image reconstruction means 209 included in the data processing unit 60 re-calibrates a corrected image and displays it on the display device 68 or the like.

According to the third embodiment, an accurate correction coefficient can be calculated using the phantom 330 having an annular (sector) section and a uniform thickness and being employed in the second embodiment.

Fourth Embodiment

Figure 16:
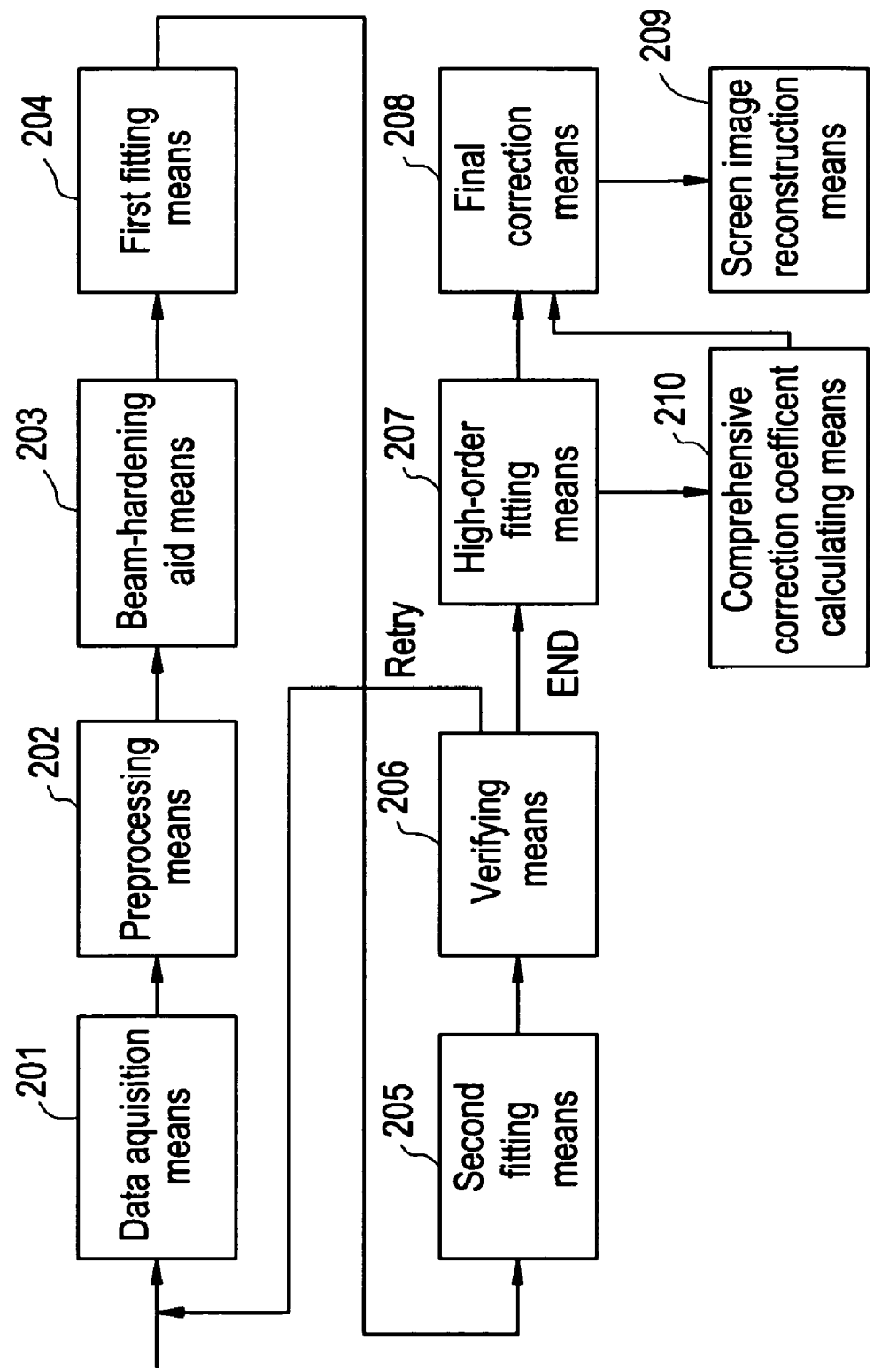
FIG. 16 shows the second configuration of the data processing unit included in the X-ray CT system illustrated in FIG. 1.

According to a fourth embodiment, correction coefficients calculated using various phantoms 310 having circular sections at step 9 according to the first embodiment, and correction coefficients calculated using various phantoms 320 having oblong sections at step 9 according to the second embodiment are used to obtain a comprehensive common correction coefficient. Therefore, as illustrated in FIG. 16, a comprehensive correction coefficient calculating means 210 is added to the data processing unit 60.

A method of calculating a comprehensive correction coefficient which is implemented in the comprehensive correction coefficient calculating means 210 is to average correction coefficients calculated using various phantoms 310 having circular sections and correction coefficients calculated using various phantoms 320 having oblong sections. Otherwise, the correction coefficients may be multiplied by predetermined weighting coefficients and then summated.

A comprehensive correction coefficient thus calculated by the comprehensive correction coefficient calculating means 210 is preserved in the storage device 66, and the final correction means 208 uses the comprehensive correction coefficient to correct projection information.

According to the fourth embodiment, a correction coefficient widely adaptable to subjects offering various conditions can be calculated. Using the correction coefficient, projection information can be corrected accurately.

Fifth Embodiment

According to a fifth embodiment, unlike the fourth embodiment, the comprehensive correction coefficient calculating means 210 illustrated in FIG. 16 uses correction coefficients that are calculated using various phantoms 310 having circular sections at step 9 according to the first embodiment, and correction coefficients, which are calculated using the phantoms 330 having annular (sector) sections and uniform thicknesses at step 9 according to the second embodiment, to calculate a comprehensive common correction coefficient.

A method of calculating a comprehensive correction coefficient which is implemented in the comprehensive correction coefficient calculating means 210 is to average the correction coefficients calculated using various phantoms 310 having circular sections and the correction coefficient calculated using the phantom 330 having an annular (sector) section and a uniform thickness. Otherwise, the correction coefficients may be multiplied by predetermined weighting coefficients and then summated.

The comprehensive correction coefficient thus calculated by the comprehensive correction coefficient calculating means 210 is preserved in the storage device 66, and the final correction means 208 uses the comprehensive correction coefficient to correct projection information.

According to the fifth embodiment, a correction coefficient widely adaptable to subjects offering various conditions can be calculated. Using the correction coefficient, projection information can be corrected accurately.

Sixth Embodiment

According to a sixth embodiment, unlike the fourth and fifth embodiments, the comprehensive correction coefficient calculating means 210 illustrated in FIG. 16 uses correction coefficients that are calculated using various phantoms 320 having oblong sections at step 9 according to the first embodiment, and correction coefficients, which are calculated using the phantoms 330 having annular (sector) sections and uniform thicknesses at step 9 according to the second embodiment, to calculate a comprehensive common correction coefficient.

A method of calculating a comprehensive correction coefficient which is implemented in the comprehensive correction coefficient calculating means 210 is to average the correction coefficients calculated using various phantoms 320 having oblong sections and the correction coefficient calculated using the phantom 330 having an annular (sector) section and a uniform thickness. Otherwise, the correction coefficients may be multiplied by predetermined weighting coefficients and then summated.

The comprehensive correction coefficient thus calculated by the comprehensive correction coefficient calculating means 210 is preserved in the storage device 66, and the final correction means 208 uses the comprehensive correction coefficient to correct projection information.

According to the sixth embodiment, a correction coefficient widely adaptable to subjects offering various conditions can be calculated. Using the correction coefficient, projection information can be corrected accurately.

Seventh Embodiment

According to a seventh embodiment, the comprehensive correction coefficient calculating means 210 illustrated in FIG. 16 uses a correction coefficient calculated using the phantom 310 having a circular section at step 9 according to the first embodiment, a correction coefficient calculated using the phantom 320 having an oblong section at step 9 according to the second embodiment, and correction coefficients calculated using the phantoms 330 having annular (sector) sections and uniform thicknesses at step 9 according to the third embodiment to calculate a common comprehensive correction coefficient.

A method of calculating a comprehensive correction coefficient which is implemented in the comprehensive correction coefficient calculating means 210 is to average the correction coefficient calculated using the phantom 310 having a circular section, the correction coefficient calculated using the phantom 320 having an oblong section, and the correction coefficient calculated using the phantom 330 having an annular (sector) section and a uniform thickness. Otherwise, the correction coefficients may be multiplied by predetermined weighting coefficients and then summated.

The comprehensive correction coefficient thus calculated by the comprehensive correction coefficient calculating means 210 is preserved in the storage device 66, and the final correction means 208 uses the comprehensive correction coefficient to correct projection information.

According to the seventh embodiment, a correction coefficient widely adaptable to subjects offering various conditions can be calculated. Using the correction coefficient, projection information can be corrected accurately.

Many widely different embodiments of the invention may be configured without departing from the spirit and the scope of the present invention. It should be understood that the present invention is not limited to the specific embodiments described in the specification, except as defined in the appended claims.

The invention claimed is:

1. A correction coefficient calculating method for X-ray CT systems, comprising the steps of:
    positioning a phantom, which has an oblong section, in a scan field between an X-ray tube and an X-ray detector, and scanning the phantom from plural directions so as to acquire a plurality of views; and
    calculating a final correction coefficient, which is used to correct projection information to be acquired from a subject, using a plurality of results of the scan; and
    determining a first correction coefficient and a second correction coefficient, wherein said calculating the final correction coefficient comprises computing the final correction coefficient from the first and second correction coefficients, wherein the first coefficient is calculated from a phantom having a first shape different than a second shape of a phantom used to calculate the second correction coefficient.

2. A correction coefficient calculating method for X-ray CT systems of claim 1, wherein the final correction coefficient is calculated as an average between the first correction coefficient and the second correction coefficient.

3. A correction coefficient calculating method for X-ray CT systems of claim 1 further comprising:
    weighting the first coefficient to generate a first weighted coefficient;
    weighting the second coefficient to generate a second weighted coefficient; and
    summing the first and second weighted coefficients.

4. A correction coefficient calculating method for X-ray CT systems of claim 1, wherein the first shape is circular and the second shape is oblong.

5. A correction coefficient calculating method for X-ray CT systems of claim 1, wherein the first shape is circular and the second shape is annular.

6. A correction coefficient calculating method for X-ray CT systems of claim 1, wherein the first shape is oblong and the second shape is annular.

7. A beam-hardening post-processing method for X-ray CT systems, comprising the steps of:
    positioning a phantom, which has an oblong section, in a scan field between an X-ray tube and an X-ray detector, scanning the phantom from one or plural directions so as to acquire a plurality of views, and producing one sinogram using first projection information;
    correcting the first projection information in terms of a beam-hardening effect so as to produce second projection information;
    fitting a first function to the second projection information so as to produce third projection information;
    fitting a second function to a plurality of third projection information values, the third projection information values being provided as functions having as independent variables a plurality of second projection information values that are sampled in relation to all the views and each of a plurality of channels of said X-ray detector constituting the second projection information; and
    correcting projection information acquired from a subject, who is positioned in the scan field, using a correction function obtained as the second function.

8. An X-ray CT system including a phantom having an oblong section positioned in a scan field between an X-ray tube and an X-ray detector, said X-ray CT system configured to:
    scan the phantom from one or plural directions to acquire a plurality of views, and produce one sinogram using first projection information;
    correct the first projection information in terms of a beam-hardening effect to produce second projection information;
    fit a first function to the second projection information to produce third projection information;
    fit a second function to a pluarity of third projection information values, the third projection information values being provided as functions having as independent variables a plurality of second projection information values that are sampled in relation to all the views and each of a plurality of channels of said X-ray detector constituting the second projection information; and
    correct projection information acquired from a subject, who is positioned in the scan field, using a correction function obtained as the second function.

* * * * *